(12) United States Patent
Hart

(10) Patent No.: US 9,254,148 B2
(45) Date of Patent: Feb. 9, 2016

(54) LOW-PROFILE SURGICAL UNIVERSAL ACCESS PORT

(75) Inventor: Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 158 days.

(21) Appl. No.: 13/462,330

(22) Filed: May 2, 2012

(65) Prior Publication Data

US 2012/0283518 A1 Nov. 8, 2012

Related U.S. Application Data

(60) Provisional application No. 61/481,366, filed on May 2, 2011.

(51) Int. Cl.
*A61B 1/32* (2006.01)
*A61B 17/34* (2006.01)

(52) U.S. Cl.
CPC ......... *A61B 17/3498* (2013.01); *A61B 17/3462* (2013.01); *A61B 17/3421* (2013.01)

(58) Field of Classification Search
CPC ........... A61B 17/3421; A61B 17/3439; A61B 17/3462; A61B 17/3498; A61B 2017/3433; A61B 2017/3443; A61B 2017/3445; A61B 2017/3464; A61B 2017/3466; A61B 2017/347; A61M 39/06; A61M 39/0613; A61M 39/1055; A61M 2039/0626; A61M 2039/066; A61M 2039/1027; A61M 25/0662
USPC ................. 600/201, 203–208, 215, 226–228; 604/164.01, 164.02, 164.04, 164.11, 604/167.01, 167.03–167.06, 248, 236, 32, 604/45; 606/185

See application file for complete search history.

(56) References Cited

U.S. PATENT DOCUMENTS

| RE682 E | 4/1859 | Peale |
|---|---|---|
| 184,573 A | 11/1876 | Becker |

(Continued)

FOREIGN PATENT DOCUMENTS

| BE | 1 006 811 | 12/1994 |
|---|---|---|
| CA | 2 170 841 | 9/1997 |

(Continued)

OTHER PUBLICATIONS

European Patent Office, Invitation to Pay Additional Fees for International Application No. PCT/US2012/036119, entitled "Low-Profile Surgical Universal Access Port", mailed Jul. 13, 2012.

(Continued)

*Primary Examiner* — Kevin T Truong
*Assistant Examiner* — Tracy Kamikawa
(74) *Attorney, Agent, or Firm* — Rimas T. Lukas

(57) ABSTRACT

A surgical access device includes an elongate cannula having a side wall at the proximal end that is coaxial with and movable relative to a seal-housing. A seal assembly that includes at least one seal is disposed within the seal-housing. An inflation port is formed in on the seal housing and configured to align with an opening in the side wall at the proximal end of the cannula. The seal housing is movable relative to the side wall between an open and closed configuration. In an open configuration, the inflation port is aligned with the opening in the side wall permitting fluid to flow across the cannula side wall. In a closed configuration, the inflation fort is offset from the opening in the side wall preventing fluid flow across the cannula side wall. In one variation, a resilient retention member is disposed inside the seal housing to bias the seal.

20 Claims, 15 Drawing Sheets

(56) References Cited

U.S. PATENT DOCUMENTS

| | | |
|---|---|---|
| 207,932 A | 9/1878 | Alvord |
| 224,513 A | 2/1880 | Burdon |
| 396,754 A | 1/1889 | Mayfield |
| 764,322 A | 7/1904 | Wiegand |
| 1,147,408 A | 7/1915 | Kelis |
| 1,672,258 A | 6/1928 | Hippenmeyer |
| 1,727,495 A | 9/1929 | Wappler |
| 1,845,727 A | 2/1932 | Slaughter |
| 2,102,274 A | 12/1937 | Larimore |
| 2,189,343 A | 2/1940 | Fritz |
| 2,301,338 A | 11/1942 | Smith |
| 2,434,594 A | 1/1948 | Schultz |
| 2,441,143 A | 5/1948 | Gracey |
| 2,646,701 A | 7/1953 | Lietin |
| 2,699,770 A | 1/1955 | Fourestier et al. |
| 2,764,148 A | 9/1956 | Sheldon |
| 2,764,149 A | 9/1956 | Sheldon |
| 2,769,355 A | 11/1956 | Henry |
| 2,877,368 A | 3/1959 | Sheldon |
| 2,932,294 A | 4/1960 | Fourestier et al. |
| 3,005,468 A | 10/1961 | Erwin et al. |
| 3,021,834 A | 2/1962 | Sheldon |
| 3,033,226 A | 5/1962 | Allen |
| 3,042,022 A | 7/1962 | Sheldon |
| 3,224,320 A | 12/1965 | Knudsen |
| 3,277,922 A | 10/1966 | Eisel |
| 3,279,460 A | 10/1966 | Sheldon |
| 3,357,433 A | 12/1967 | Fourestier et al. |
| 3,385,553 A | 5/1968 | Braun |
| 3,417,745 A | 12/1968 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,791,379 A | 2/1974 | Storz |
| 3,817,251 A | 6/1974 | Hasson |
| 3,821,956 A | 7/1974 | Gordhamer |
| 3,870,036 A | 3/1975 | Fiore |
| 3,961,621 A | 6/1976 | Northeved |
| 3,971,385 A | 7/1976 | Corbett |
| 3,994,287 A | 11/1976 | Turp |
| 3,994,301 A | 11/1976 | Agris |
| 4,028,987 A | 6/1977 | Wilson |
| 4,112,932 A | 9/1978 | Chiulli |
| 4,126,291 A | 11/1978 | Gilbert et al. |
| 4,150,929 A | 4/1979 | Brandt |
| 4,168,882 A | 9/1979 | Hopkins |
| 4,180,068 A | 12/1979 | Jacobsen et al. |
| 4,191,191 A | 3/1980 | QAubum |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,274,771 A | 6/1981 | Nishimura |
| 4,285,618 A | 8/1981 | Shanley |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,386,179 A | 5/1983 | Sterling |
| 4,414,966 A | 11/1983 | Stednitz |
| 4,429,856 A | 2/1984 | Jackson |
| 4,436,519 A | 3/1984 | O'Neill |
| 4,493,444 A | 1/1985 | Deli et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,750,877 A | 6/1988 | McFarlane |
| 4,762,130 A | 8/1988 | Fogarty et al. |
| 4,779,613 A | 10/1988 | Hashiguchi et al. |
| 4,803,999 A | 2/1989 | Liegner |
| 4,813,400 A | 3/1989 | Washizuka et al. |
| 4,850,393 A | 7/1989 | Lashomb |
| 4,895,431 A | 1/1990 | Tsujluchi et al. |
| 4,901,142 A | 2/1990 | Ikuno et al. |
| 4,917,668 A * | 4/1990 | Haindl .................... 604/167.03 |
| 4,956,143 A | 9/1990 | McFarlane |
| 4,959,067 A | 9/1990 | Muller |
| 4,972,827 A | 11/1990 | Kishi et al. |
| 4,978,350 A | 12/1990 | Wagenknecht |
| 5,017,057 A | 5/1991 | Kruygor |
| 5,030,210 A | 7/1991 | Alchas |
| 5,041,100 A | 8/1991 | Rowland et al. |
| 5,057,082 A | 10/1991 | Burchette, Jr. |
| 5,066,288 A | 11/1991 | Deniego et al. |
| 5,098,379 A | 3/1992 | Conway |
| 5,098,388 A | 3/1992 | Kulkashi et al. |
| 5,104,316 A | 4/1992 | McSpadden |
| 5,104,388 A | 4/1992 | Quackenbush |
| 5,104,389 A | 4/1992 | Deem et al. |
| 5,114,407 A | 5/1992 | Burbank |
| 5,116,547 A | 5/1992 | Tsukahara et al. |
| 5,147,376 A | 9/1992 | Pianetti |
| 5,159,920 A | 11/1992 | Condon et al. |
| 5,163,941 A | 11/1992 | Garth et al. |
| 5,178,186 A | 1/1993 | Levasseur |
| 5,186,972 A | 2/1993 | Williams et al. |
| 5,197,955 A | 3/1993 | Stephens et al. |
| 5,207,656 A | 5/1993 | Kranys |
| 5,217,441 A | 6/1993 | Shichman |
| 5,221,163 A | 6/1993 | Nishimura |
| 5,240,397 A | 8/1993 | Fay et al. |
| 5,246,425 A | 9/1993 | Hunsberger et al. |
| 5,250,068 A | 10/1993 | Ideguchi et al. |
| 5,256,149 A | 10/1993 | Banik et al. |
| 5,258,003 A | 11/1993 | Ciaglia |
| 5,269,316 A | 12/1993 | Spitainy |
| 5,269,771 A * | 12/1993 | Thomas et al. ............... 604/539 |
| 5,271,380 A | 12/1993 | Riek et al. |
| 5,279,567 A | 1/1994 | Ciaglia et al. |
| 5,288,290 A | 2/1994 | Brody |
| 5,290,276 A | 3/1994 | Sewell |
| 5,290,585 A | 3/1994 | Elton |
| 5,300,033 A | 4/1994 | Miller |
| 5,334,150 A | 8/1994 | Kaali |
| 5,342,382 A | 8/1994 | Brinkerhoff |
| 5,350,364 A | 9/1994 | Stephens et al. |
| 5,370,624 A | 12/1994 | Edwards et al. |
| 5,372,588 A | 12/1994 | Farley |
| 5,374,253 A | 12/1994 | Burns, Sr. et al. |
| 5,380,291 A | 1/1995 | Kaali |
| 5,387,197 A | 2/1995 | Smith |
| 5,389,077 A | 2/1995 | Melinyshyn et al. |
| 5,391,153 A | 2/1995 | Haber et al. |
| 5,391,248 A | 2/1995 | Brain |
| 5,392,766 A | 2/1995 | Masterson et al. |
| 5,405,328 A | 4/1995 | Vidal et al. |
| 5,407,427 A | 4/1995 | Zhu et al. |
| 5,431,151 A | 7/1995 | Riek et al. |
| 5,441,041 A | 8/1995 | Sauer et al. |
| 5,443,484 A | 8/1995 | Kirsch et al. |
| 5,445,615 A | 8/1995 | Yoon et al. |
| 5,454,791 A | 10/1995 | Tovey et al. |
| 5,480,410 A | 1/1996 | Cuschieri et al. |
| 5,510,065 A | 4/1996 | McFarlane |
| 5,540,711 A | 7/1996 | Kieturakis et al. |
| 5,542,845 A | 8/1996 | Jenkins |
| 5,549,546 A | 8/1996 | Schneider et al. |
| 5,551,947 A | 9/1996 | Kaai |
| 5,562,696 A | 10/1996 | Nobles et al. |
| 5,569,291 A | 10/1996 | Privitera |
| 5,569,292 A | 10/1996 | Scwemberger et al. |
| 5,577,993 A | 11/1996 | Zhu et al. |
| 5,591,186 A | 1/1997 | Wurster et al. |
| 5,591,192 A | 1/1997 | Privitera et al. |
| 5,593,402 A | 1/1997 | Patrick |
| 5,603,720 A | 2/1997 | Kieturakis |
| 5,609,562 A | 3/1997 | Kaali |
| 5,609,604 A | 3/1997 | Schwemberger et al. |

(56) References Cited

U.S. PATENT DOCUMENTS

| | | |
|---|---|---|
| 5,613,954 A | 3/1997 | Nelson et al. |
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Domandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,785,693 A | 7/1998 | Halninig |
| 5,792,112 A | 8/1998 | Hart et al. |
| 5,797,888 A | 8/1998 | Yoon et al. |
| 5,797,944 A | 8/1998 | Nobeles et al. |
| 5,817,061 A | 10/1998 | Goodwin et al. |
| 5,817,062 A | 10/1998 | Flom et al. |
| 5,836,957 A | 11/1998 | Shulz |
| 5,842,971 A | 12/1998 | Yoon |
| 5,860,996 A | 1/1999 | Urban et al. |
| 5,871,474 A | 2/1999 | Hermann et al. |
| 5,876,202 A | 3/1999 | Berlin |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpapa et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,656,160 B1 | 12/2003 | Taylor et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs |
| 7,344,519 B2 | 3/2008 | Wing et al. |
| 7,370,709 B2 | 5/2008 | Williamson, Jr. |
| 7,470,255 B2 | 12/2008 | Sterns et al. |
| 7,563,250 B2 | 7/2009 | Wenchell |
| 7,686,823 B2 | 3/2010 | Pingleton et al. |
| 7,708,713 B2 | 5/2010 | Albrecht et al. |
| 7,758,603 B2 | 7/2010 | Taylor et al. |
| 7,794,644 B2 | 9/2010 | Taylor et al. |
| 7,803,135 B2 * | 9/2010 | Franer ...................... 604/164.01 |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,105,285 B2 | 1/2012 | Hart et al. |
| 8,152,828 B2 | 4/2012 | Taylor et al. |
| 8,282,663 B2 | 10/2012 | Smith |
| 8,317,815 B2 | 11/2012 | Mastri et al. |
| 8,353,874 B2 * | 1/2013 | Okoniewski ............. 604/167.03 |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 | 12/2002 | Tsonton et al. |
| 2003/0023201 A1 | 1/2003 | Aboul-Hosn |
| 2003/0032755 A1 | 2/2003 | Gomey et al. |
| 2003/0059263 A1 | 3/2003 | Chen |
| 2003/0187471 A1 | 10/2003 | Cooper |
| 2004/0015185 A1 | 1/2004 | Ewers et al. |
| 2004/0082969 A1 | 4/2004 | Kerr |
| 2004/0093000 A1 | 5/2004 | Kerr |
| 2004/0093018 A1 | 5/2004 | Johnson et al. |
| 2004/0106942 A1 | 6/2004 | Taylor et al. |
| 2004/0108623 A1 | 6/2004 | Deeter et al. |
| 2004/0167559 A1 | 8/2004 | Taylor et al. |
| 2004/0199127 A1 | 10/2004 | Jensen et al. |
| 2004/0204671 A1 | 10/2004 | Stubbs et al. |
| 2004/0230155 A1 | 11/2004 | Blanco et al. |
| 2004/0230217 A1 | 11/2004 | O'Heeroon |
| 2004/0254517 A1 | 12/2004 | Quiroz-Mercado et al. |
| 2005/0033237 A1 | 2/2005 | Fentress et al. |
| 2005/0033246 A1 | 2/2005 | Ahlberg et al. |
| 2005/0038466 A1 | 2/2005 | O'Heeron et al. |
| 2005/0059865 A1 | 3/2005 | Kahle |
| 2005/0065543 A1 | 3/2005 | Kahle et al. |
| 2005/0070850 A1 | 3/2005 | Albrecht |
| 2005/0107803 A1 | 5/2005 | Guanche |
| 2005/0107816 A1 | 5/2005 | Pingleton et al. |
| 2005/0113533 A1 | 5/2005 | Shaikh et al. |
| 2005/0149094 A1 | 7/2005 | Kashara et al. |
| 2005/0149096 A1 | 7/2005 | Hilal et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0273133 A1 | 12/2005 | Schluzas et al. |
| 2005/0283122 A1 | 12/2005 | Nordgren |
| 2005/0288622 A1 | 12/2005 | Albrecht et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0058570 A1 | 3/2006 | Rapach et al. |
| 2006/0074374 A1 | 4/2006 | Gresham |
| 2006/0118189 A1 | 6/2006 | Trekulve et al. |
| 2006/0224174 A1 | 10/2006 | Smith et al. |
| 2006/0264991 A1 | 11/2006 | Johnson |

(56) References Cited

U.S. PATENT DOCUMENTS

| | | | |
|---|---|---|---|
| 2007/0027453 | A1 | 2/2007 | Hart et al. |
| 2007/0075465 | A1 | 4/2007 | Taylor et al. |
| 2007/0088277 | A1 | 4/2007 | McGinley |
| 2007/0239108 | A1 | 10/2007 | Albrecht et al. |
| 2008/0065021 | A1 | 3/2008 | Jenkins et al. |
| 2008/0086074 | A1 | 4/2008 | Taylor et al. |
| 2008/0086093 | A1 | 4/2008 | Steppe et al. |
| 2009/0137943 | A1 | 5/2009 | Stearns et al. |
| 2010/0025045 | A1 | 2/2010 | Lake et al. |
| 2010/0179479 | A1* | 7/2010 | Albrecht et al. ......... 604/167.01 |
| 2010/0240958 | A1* | 9/2010 | Abrams et al. ................ 600/201 |
| 2010/0249708 | A1* | 9/2010 | Bettuchi .................. 604/167.01 |

FOREIGN PATENT DOCUMENTS

| | | |
|---|---|---|
| DE | 0365049 | 12/1922 |
| DE | 1616107 | 4/1971 |
| DE | 2218901 | 10/1973 |
| DE | 2538758 | 3/1977 |
| DE | 2929233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| DE | 29521431 | 4/1997 |
| DE | 195 41 041 | 5/1997 |
| DE | 19541041 | 5/1997 |
| DE | 19718086 | 11/1998 |
| DE | 198 19 432 | 11/1999 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 548612 | 6/1993 |
| EP | 0556056 | 8/1993 |
| EP | 0724864 | 8/1996 |
| EP | 1582158 | 10/2005 |
| EP | 2229897 | 9/2010 |
| EP | 2233090 | 9/2010 |
| FR | 1370580 | 8/1964 |
| GB | 2 124 970 | 2/1984 |
| GB | 186 005 | 9/1992 |
| GB | 2 313 316 | 11/1997 |
| JP | 08127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 96/01132 | 1/1996 |
| WO | WO 96/10361 | 4/1996 |
| WO | WO 97/40758 | 11/1997 |
| WO | WO 98/33536 | 8/1998 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 01/08563 | 2/2001 |
| WO | WO 02/01998 | 1/2002 |
| WO | WO 02/34108 | 5/2002 |
| WO | WO 03/026512 | 4/2003 |
| WO | WO 03/032819 | 4/2003 |
| WO | WO 03/096879 | 11/2003 |
| WO | WO 2004/037097 | 5/2004 |
| WO | WO 2004/093699 | 11/2004 |
| WO | WO 2005/063134 | 7/2005 |
| WO | WO 2007/093957 | 8/2007 |

OTHER PUBLICATIONS

U.S. Appl. No. 10/745,262, filed Dec. 23, 2003; Title: "Catheter With Conduit Traversing Tip" (abandoned).

Co-Pending U.S. Appl. No. 12/750,372, filed Mar. 30, 2010, title: "Bladeless Obturator".

Co-Pending U.S. Appl. No. 11/549,872, filed Oct. 16, 2006, title: "Surgical Devices, Systems and Methods Thereof Having Gel Material, Gel Coatings, or Gel Lubricants".

Co-Pending U.S. Appl. No. 13/565,972, filed Aug. 3, 2012, title: "Bladeless Optical Obturator".

Co-Pending U.S. Appl. No. 13/356,260, filed Jan. 23, 2012, title: "Insufflating Optical Surgical Instrument".

Co-Pending U.S. Appl. No. 13/078,750, filed Apr. 1, 2011 title "Surgical Access Apparatus and Method".

Co-Pending U.S. Appl. No. 12/569,652, filed Sep. 29, 2009; title "First-Entry Trocar System".

Co-Pending U.S. Appl. No. 12/359,964, filed Jan. 26, 2009, title: "Insufflating Access System".

Co-Pending U.S. Appl. No. 13/462,330, filed May 2, 2012, title: "Low-Profile Surgical Universal Access Port".

Co-Pending U.S. Appl. No. 13/411,244, filed Mar. 2, 2012, title: "Blunt Tip Obturator".

Co-Pending U.S. Appl. No. 13/586,825, filed Aug. 15, 2012, title: "Blunt Tip Obturator".

Co-Pending U.S. Appl. No. 11/868,883, filed Oct. 8, 2007; Title: "Visual Insufflation Port".

International Bureau of WIPO, International Preliminary Report on Patentability for International Application No. PCT/US04/032346, dated May 20, 2008.

International Bureau of WIPO, International Preliminary Report on Patentability for International Application No. PCT/US2005/022716 mailed Nov. 22, 2005.

International Bureau of WIPO, International Preliminary Report on Patentability for International Application No. PCT/US2006/060013, mailed Apr. 24, 2008.

International Bureau of WIPO, The International Preliminary Report on Patentability for International Application No. PCT/US2009/058792, titled First Entry Trocar System, dated Mar. 29, 2011.

International Bureau of WIPO, The International Preliminary Report on Patentability for International Application No. PCT/US2007/080724, titled "Visual Insufflation Port", dated Apr. 7, 2009.

International Bureau of WIPO, The International Preliminary Report on Patentability for International Application No. PCT/US2009/32026, titled "Insufflating Access System", dated Jul. 27, 2010.

International Bureau of WIPO, The International Preliminary Report on Patentability for International Application No. PCT/US2004/000695, titled "Surgical Access Apparatus and Method", dated Jul. 22, 2005.

International Bureau of WIPO, The International Preliminary Report on Patentability for International Application No. PCT/US2004/04883, titled "Surgical Access Apparatus and Method", dated Sep. 9, 2005.

International Searching Authority, International Search Report and Written Opinion for International Application No. PCT/US2004/000695, titled "Surgical Access Apparatus and Method", mailed Jan. 12, 2005.

International Searching Authority, International Search Report and Written Opinion for International Application No. PCT/US2004/04883, titled "Surgical Access Apparatus and Method", mailed Mar. 31, 2005.

International Searching Authority, International Search Report and Written Opinion for International Application No. PCT/US2002/06759, titled "Bladeless Obturator", mailed Jul. 12, 2002.

International Searching Authority, International Search Report and Written Opinion for International Application No. PCT/US2005/022716, titled "Insufflating Optical Surgical Instrument", mailed Nov. 22, 2005.

International Searching Authority, International Search Report and Written Opinion for International Application No. PCT/US04/32346, titled Bladeless Optical Obturator, mailed May 20, 2008.

International Searching Authority, International Search Report and Written Opinion for International Application No. PCT/US2009/32026, titled "Insufflating Access System", mailed Mar. 23, 2009.

International Searching Authority, International Search Report and Written Opinion for International Application No. PCT/US2007/080724, titled "Visual Insufflation Port", mailed Apr. 16, 2008.

(56) References Cited

OTHER PUBLICATIONS

International Searching Authority/US, International Search Report and the Written Opinion of the International Searching Authority dated May 27, 2009, for International Application No. PCT/US2009/037863, titled "Instrument Seal with Inverting Shroud", mailed May 27, 2009.

The International Searching Authority, The International Search Report and the Written Opinion for International Application No. PCT/US2009/058792, titled "First Entry Trocar System", mailed Dec. 23, 2009.

International Searching Authority, International Search Report and Written Opinion for International Application No. PCT/US2012, title "Low-Profile Surgical Universal Access Port", mailed Nov. 7, 2012.

European Patent Office, Supplementary European Search Report for European Patent Application No. EP 02706494.8, titled "Bladeless Obturator", dated Jun. 24, 2008.

European Patent Office, Supplementary European Search Report for European Patent Application No. EP 03753017.7, titled "Blunt Tip Obturator", dated Nov. 21, 2008.

European Patent Office, Supplementary European Search Report for European Patent Application No. EP 047122378, titled "Surgical Access Apparatus and Method", dated May 19, 2008.

European Patent Office, Supplementary European Search Report for European Patent Application No. EP 07843973.4, titled "Visual Insufflation Port" dated Oct. 4, 2008.

European Patent Office, Supplementary European Search Report for European Patent Application No. EP 04793965.7, titled "Bladeless Optical Obturator", dated Apr. 16, 2010.

European Patent Office, Supplementary European Search Report for European Patent Application No. EP 11154547.1, titled "Blunt Tip Obturator", dated Mar. 22, 2011.

European Patent Office, European Search Report for European Application No. 11191191.3, titled "Bladeless Obturator" dated Feb. 29, 2012.

European Patent Office, European Search Report for European Application No. 11191179.8, titled "Bladeless Obturator", dated Feb. 21, 2012.

European Patent Office, European Search Report for European Application No. 11191193.9, titled "Bladeless Obturator", dated Mar. 5, 2012.

European Patent Office, European Search Report for European Application No. 11191187.1, titled Bladeless Obturator, dated Feb. 23, 2012.

European Patent Office, European Search Report for European Application No. 11191184.8, titled "Bladeless Obturator", dated Feb. 23, 2012.

European Patent Office, European Search Report for European Application No. 11191189.7, titled "Bladeless Obturator", dated Feb. 24, 2012.

European Patent Office, European Search Report for European Application No. 11191175.6, titled "Bladeless Obturator", dated Feb. 21, 2012.

European Patent Office, European Search Report for European Application No. 047017314, titled "Surgical Access Apparatus and Method", dated Mar. 30, 2007.

Karl Storz, The Karl Storz Ternamian EndoTIP (TM) System, date: Aug. 27, 2001.

Karl Storz, ZEROCART Trocar with eccentric tip, Recklinghausen, Germany, date Mar. 7, 2001.

Ethicon Endo-Surgery, Inc., ENDOPATH Minimally Invasive Access, date: 2001.

European Patent Office, European Search Report for European Application No. 12187933, titled "Insufflating Optical Surgical Instrument", dated Nov. 20, 2012.

European Patent Office, European Search Report for European Application No. 12187929, titled "Insufflating Optical Surgical Instrument", dated Nov. 20, 2012.

The International Bureau of WIPO, International Preliminary Report on Patentability for International Application No. PCT/US2012/036119, entitled "Low-Profile Surgical Universal Access Port", dated Nov. 5, 2013.

\* cited by examiner

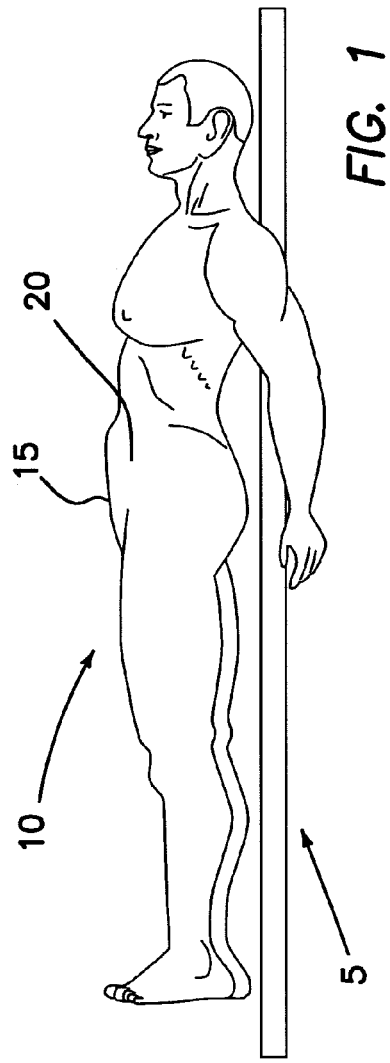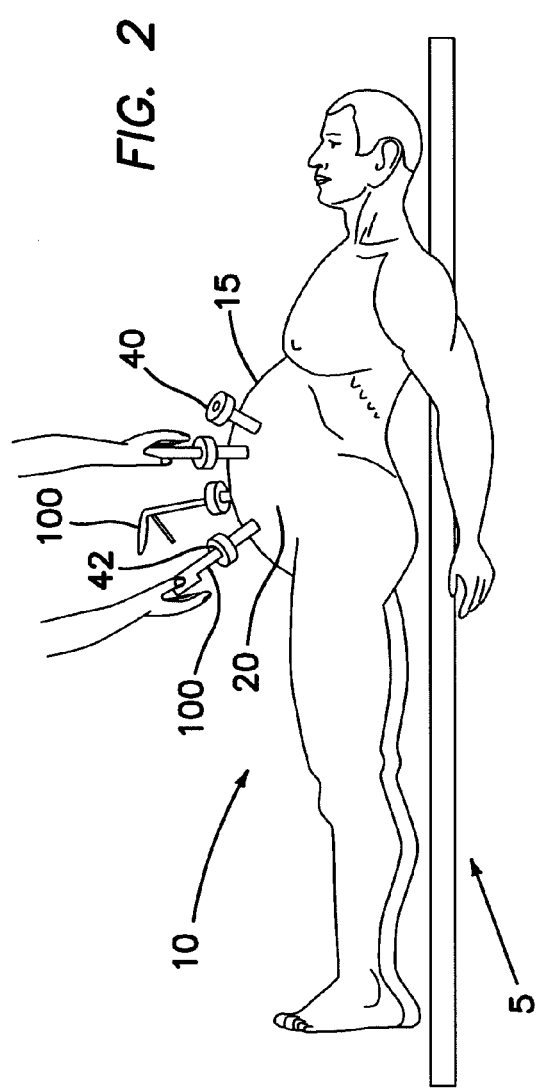

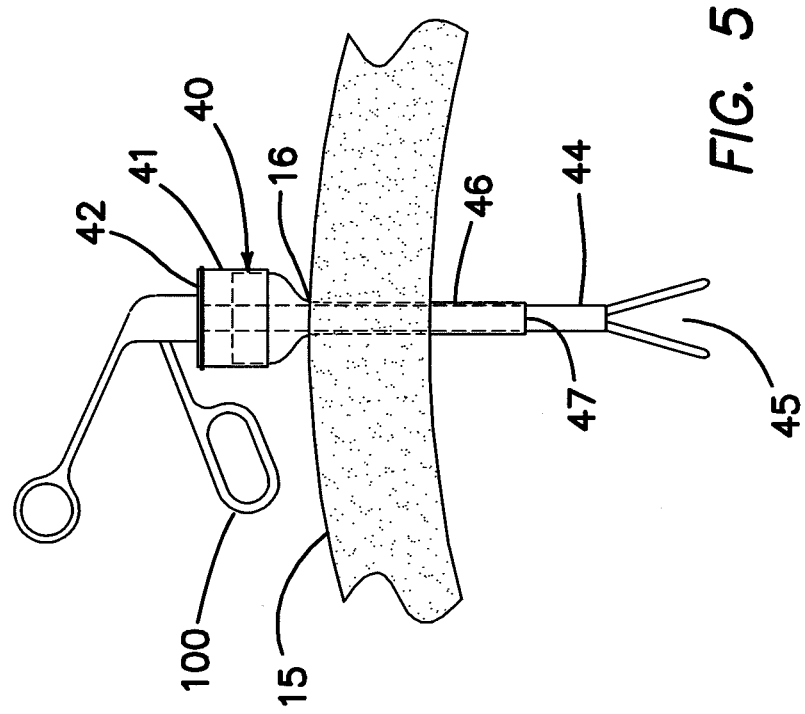
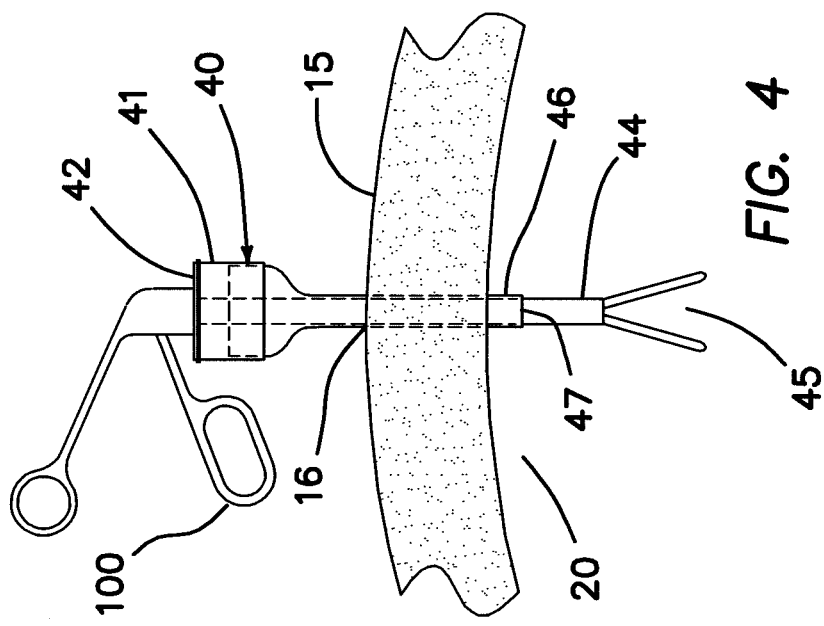

LOW-PROFILE SURGICAL UNIVERSAL ACCESS PORT

CROSS-REFERENCE TO RELATED APPLICATIONS

This application claims priority to and benefit of U.S. Provisional Patent Application Ser. No. 61/481,366 entitled "Low-profile surgical universal access port" filed on May 2, 2011 which is incorporated herein by reference in its entirety.

FIELD

This invention relates to surgical access devices, and more particularly, to trocars for use in laparoscopic, minimally invasive surgery.

BACKGROUND

One type of surgical access device is commonly referred to as a trocar. Typically, the term "trocar" is used to describe a combination of a cannula, a cannula seal housing, and an obturator. The obturator is a penetrating instrument typically associated with the cannula and inserted through the seal housing and into the lumen of the cannula to expose a penetrating tip of the obturator at the distal end. The cannula seal housing operates to maintain pneumoperitoneum pressure while instruments are inserting into the lumen of the cannula and into the abdominal cavity. The terms "access port" and "access device" are also used to refer to a trocar.

Advances in laparoscopic or minimally invasive surgery have placed new demands on access devices. Because of the increasing complexity of surgical procedures now performed laparoscopically, as well as developments in the instrumentation used in such procedures, improvements, upgrades, and/or redesigns of presently available access devices are desirable. For example, in the early years of laparoscopy, laparoscopic cholecystectomy was considered a complex procedure, which typically included placing three to five access ports and using about three different instruments. Now, laparoscopic cholecystectomy is considered routine surgery and even performed using a single incision in the patient's umbilicus. Other laparoscopic procedures include more complex surgery of the intestine, stomach, lung, uterus, spleen, liver, etc. Instruments specifically developed for such procedures are often complex and asymmetrical, and may include, for example, undercuts, side openings, and sharp regions that can damage and/or destroy a trocar seal. Procedures in which a wide range of instrument sizes are inserted through an access port produce additional issues. For instance, in some procedures instrument diameters range from about 4.5 mm to over about 15 mm. In such procedures, maintaining pneumoperitoneum pressure as small instruments are moved within a region of the seal system designed to accommodate larger instruments is challenging. Also, complex instrumentation requires more space for manipulation and a greater range of motion inside and outside the patient.

Furthermore, access ports placed in a patient may have a tendency to flop around when no instrument is inserted and consequently, when a surgeon attempts to insert an instrument into the access port, the opening of the access port is not in the appropriate position, thereby, necessitating realignment or repositioning of the access point. Other areas for improvement include constructs that secure the seal and prevent it from tearing or overlapping when instruments are inserted and removed. The present invention provides a new and improved trocar that meets these needs.

SUMMARY

The present invention provides a surgical access device. The surgical access device includes an elongate tubular cannula having a lumen extending between a proximal end and a distal end. The cannula has a side wall that extends radially outwardly relative to the distal end of the cannula forming an enlarged lumen at the proximal end. The cannula includes an opening extending through the side wall at the proximal end. A seal housing is connected to and coaxial with the proximal end of the cannula and configured to be sealingly movable relative to the side wall. An inflation port extends through the seal housing and is configured to align with the opening in the side wall to fluidly connect the inflation port and opening with the cannula lumen. A seal assembly includes at least one seal disposed in the seal housing. The seal housing is movable relative to the side wall between an open configuration and a closed configuration. In the open configuration, the inflation port is in alignment with the opening in the side wall, thereby, fluidly connecting the inflation port and opening with the cannula lumen. In the closed configuration, the lumen of the inflation port is offset from the opening in side wall, thereby, fluidly isolating the inflation port from the opening in the side wall.

According to another aspect of the invention, a surgical access device is provided. The surgical access device includes an elongate tubular cannula having a lumen extending between a proximal end and a distal end. A seal housing is connected to the proximal end of the cannula. A seal assembly is disposed inside the seal housing and includes at least one seal. An access channel is defined along a longitudinal axis extending through the seal assembly and lumen of the cannula from the proximal end to the distal end. The device further includes a resilient member having a proximal end and a distal end. The resilient member is located between the seal assembly and the seal housing.

According to another aspect of the invention a method is provided. The method includes the step of moving a seal housing relative to a cannula. The seal housing is generally cylindrical and movably connected to the cannula. The cannula has a generally cylindrical side wall defining a central lumen along a longitudinal axis that is coaxial with the lumen of the seal housing. The seal housing is sealingly connected to the side wall at the proximal end of the cannula such that the seal housing can move relative to the side wall of the cannula. A seal assembly includes at least one seal and is disposed inside the seal housing at the proximal end. The seal housing includes an inflation port and the side wall of the cannula includes an opening configured such that alignment of the inflation port and opening places the cannula lumen and a plenum distal of the seal assembly into fluidic communication with outside of the cannula via the opening and outside of the seal housing via the inflation port. The seal housing is movable relative to the cannula between an open position and a closed position. In the open position, the opening and inflation port are at least on partial alignment. In the closed position, the opening and the inflation port are misaligned preventing fluidic communication across the seal housing. The method further includes the step of bringing into at least partial alignment the inflation port of the seal housing and the opening of the side wall of the cannula. Fluid is moved under pressure through the lumen of the cannula after the at least partial alignment of the inflation port of the seal housing with the opening in the side wall of the cannula. The inflation port and the opening in the side wall of the cannula are completely misaligned to shut fluidic communication across the side wall through the opening and across the seal housing through the inflation port.

According to another aspect of the invention, a surgical access device is provided. The surgical access device includes an elongate tubular cannula having a lumen extending between a proximal end and a distal end. A seal housing is connected to the proximal end of the cannula. The seal housing includes an access channel coaxial with the lumen of the cannula. The seal housing includes an outer side wall having a first opening movable relative to an inner side wall having a second opening. At least one seal is disposed inside the seal housing. The first and second openings are configured to align at least in part to fluidly connect the cannula lumen across the seal housing and configured to move completely out of alignment. The outer side wall is movable relative to the inner side wall between an open configuration and a closed configuration. In the open configuration, the first opening is in alignment at least in part with the second opening, thereby, fluidly connecting the cannula lumen across the seal housing. In the closed configuration, the first opening is offset from the second opening, thereby, closing fluidic communication across the seal housing.

BRIEF DESCRIPTION OF THE DRAWINGS

FIG. 1 is a side view of a surgical subject on an operating table in a non-insufflated state.

FIG. 2 is a side view of a surgical subject on an operating table in an insufflated state with a plurality of access devices placed in the abdomen.

FIG. 4 is a side cross-sectional view of a variation of a surgical access port placed through a body wall in a first position.

FIG. 5 is a side cross-sectional view of the surgical access port illustrated in FIG. 4 placed through a body wall in a second position.

DETAILED DESCRIPTION

Figure 3:
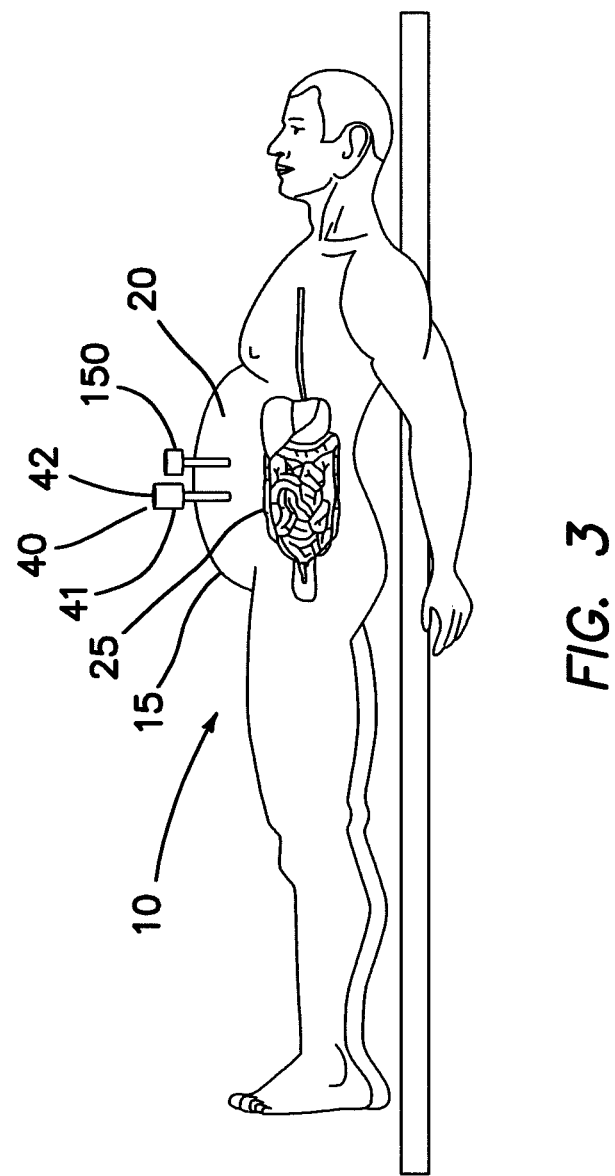
FIG. 3 is a partial cross-sectional side view of an insufflated surgical subject with a plurality of access devices placed in the abdomen.

With particular reference to FIGS. 1-3, FIG. 1 is a side view of a patient 10 placed upon a surgical table 5 in a supine position in preparation for a minimally invasive surgical procedure on the patient's abdomen 20. In FIG. 2, the abdomen 20 of the subject 10 is inflated with an insufflation gas, which distends the abdominal wall 15, thereby creating an unobstructed working area 25 within the abdomen 20, as illustrated in partial cross section in FIG. 3. Examples of suitable abdominal procedures include operations on the appendix, spleen, liver, kidneys, stomach, gall-bladder, intestinal tract, and the like. As illustrated in FIGS. 2 and 3, multiple access ports 40 are placed through the patient's abdominal wall 15 in some procedures and laparoscopic instrumentation 100 is inserted into the working lumen 42 of the access ports 40. Specialized instrumentation 100 has been developed that fit through the small working lumen 42 and also accommodate patients 10 with very thick abdominal walls 15 and/or vast abdominal cavities 20.

Compatibility with the full range of existing laparoscopic instrumentation is often compromised because of a length of the access device 40. For example, as illustrated in FIG. 3, a long and/or tall seal housing 41 relative to a shorter, low-profile access port 150 limits the operational range of some instruments 100 inserted therein. Furthermore, access devices 40 that are long and/or tall, and extend out from the external abdominal wall 15 tend to flop over and/or fail to remain in preferred positions. Furthermore, a misaligned access port 40 is typically positioned and/or stabilized by an additional hand, either the surgeon's or an assistant's, before guiding the instrument 100 into the working lumen 42 of the device 40.

Figure 6:
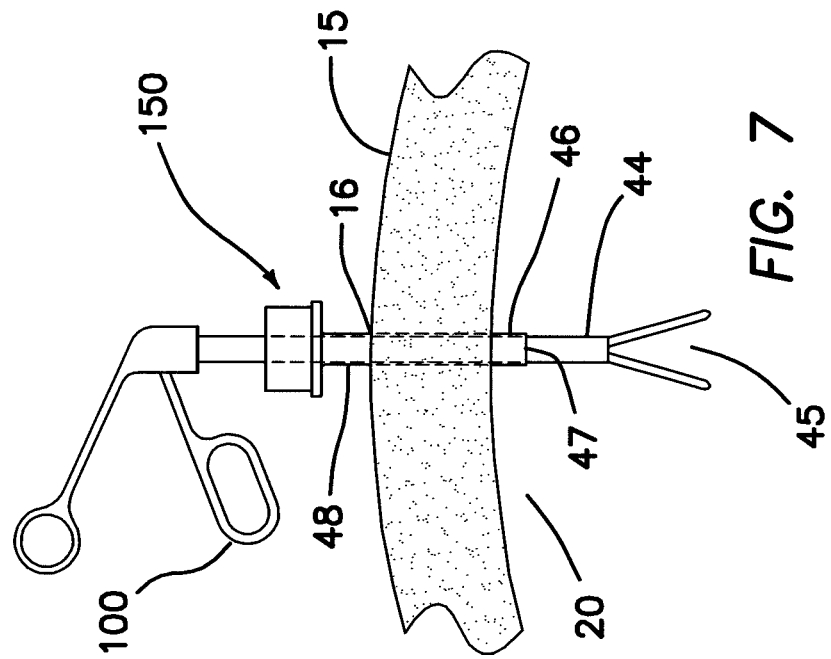
FIG. 6 is a side cross-sectional view of the surgical access port illustrated in FIG. 4 with an instrument fully extended therethrough.
Figure 7:
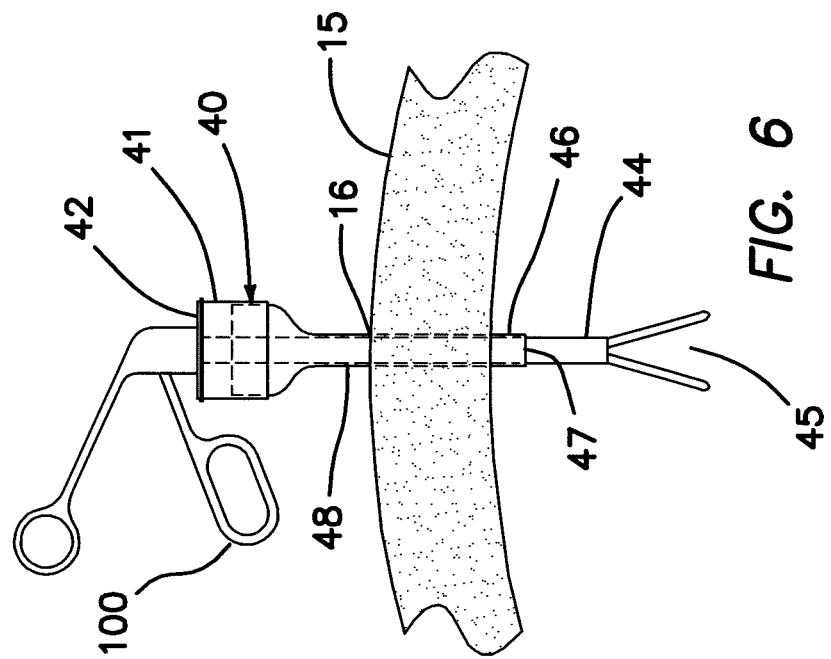
FIG. 7 is a side cross-sectional view of a surgical access port according to the present invention with an instrument fully extended therethrough.
Figure 9:
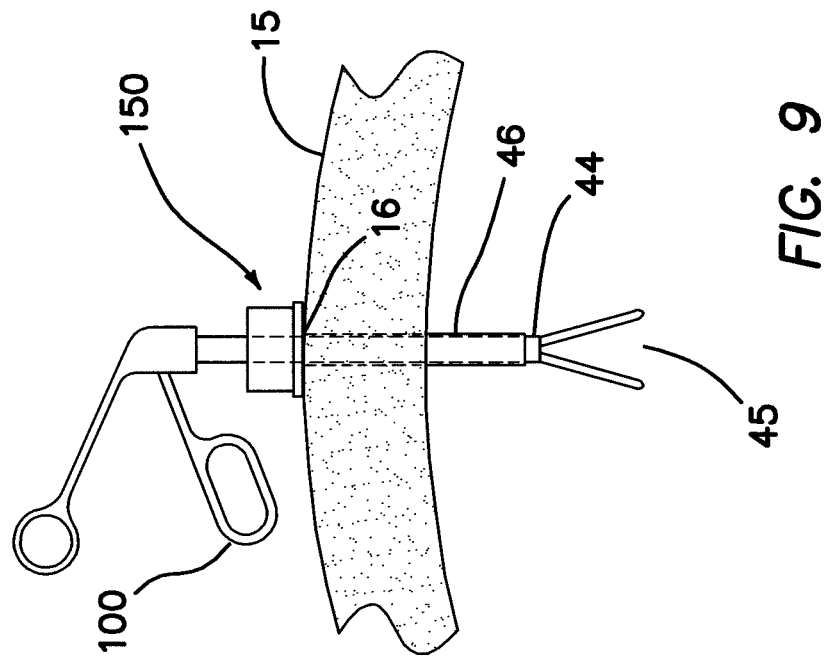
FIG. 9 is a side view of the variation of the surgical access port illustrated in FIG. 7 in an extreme forward condition showing an extended instrument range according to the present invention.
Figure 8:
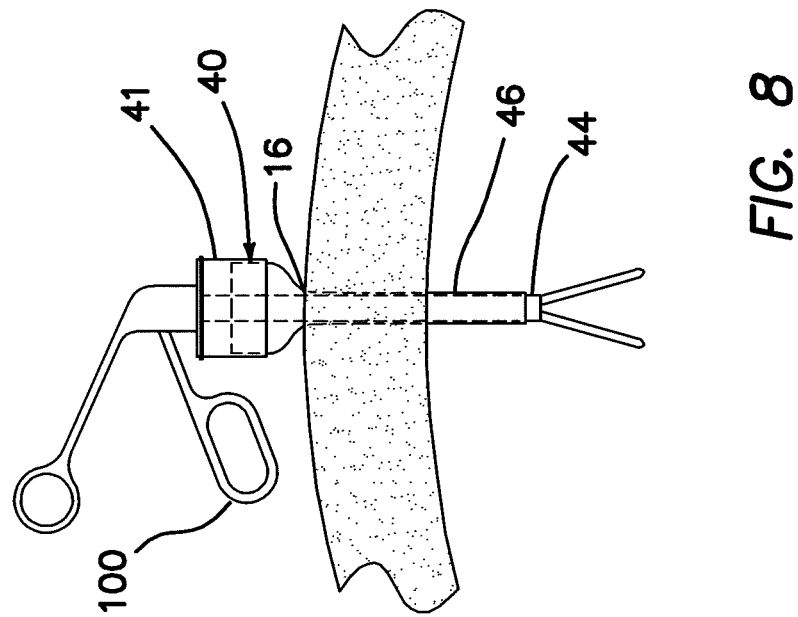
FIG. 8 is a side view of the variation of the surgical access port illustrated in FIG. 4 in an extreme forward condition.
Figures 10, 11:
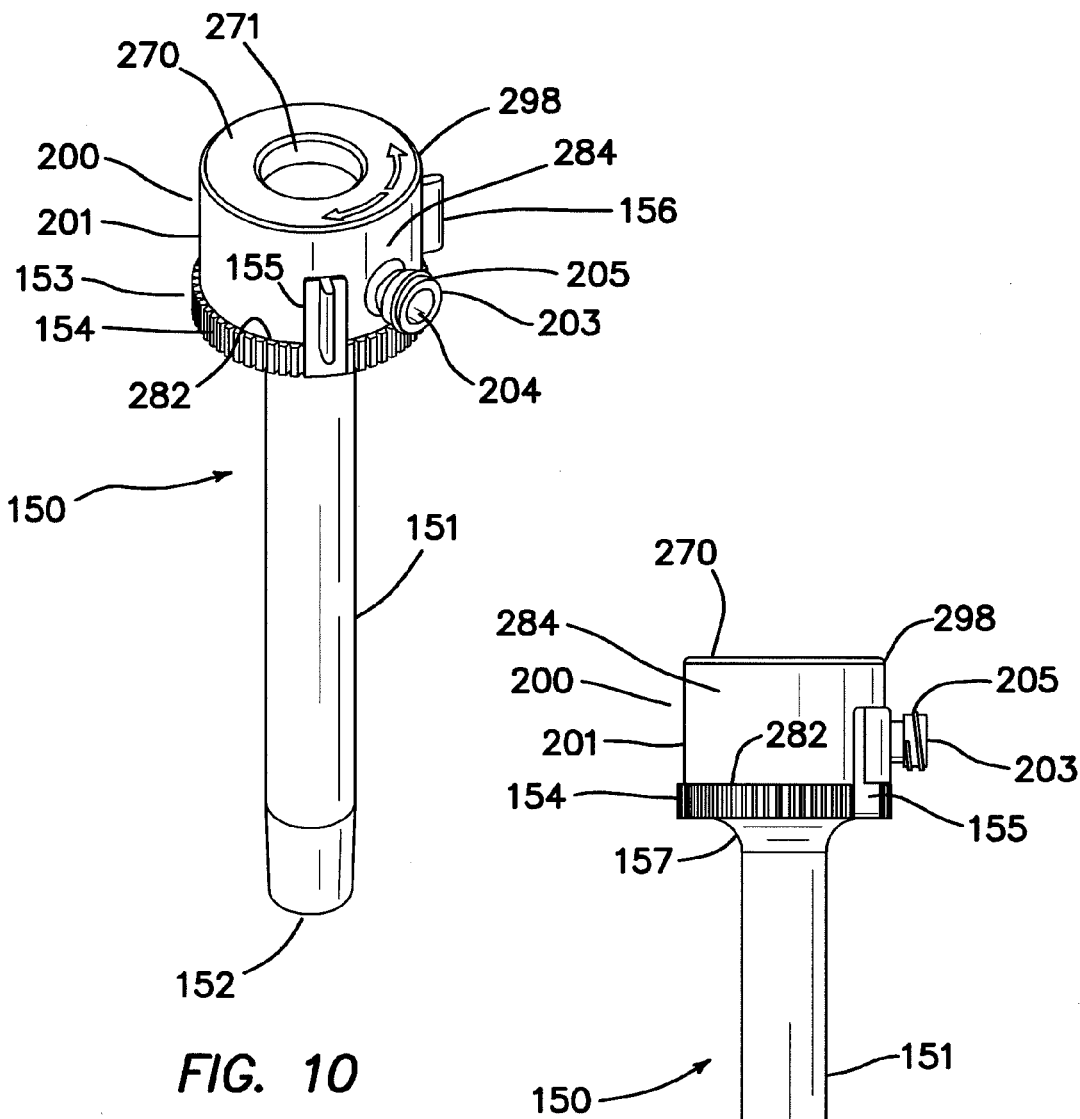
FIG. 10 is a perspective view of a surgical access port according to the present invention.
FIG. 11 is a side view of a surgical access port according to the present invention.
Figure 12:
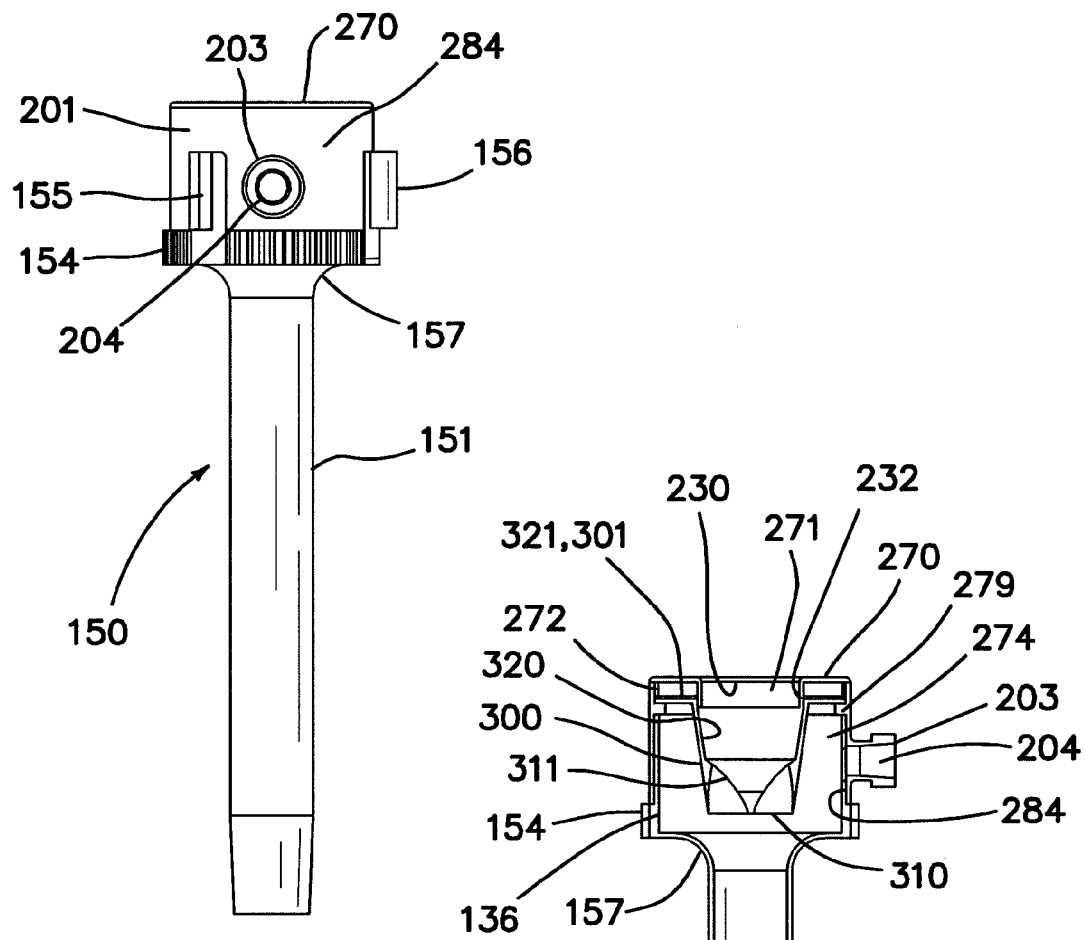
FIG. 12 is a front view of a surgical access port according to the present invention.

FIG. 4 is a side view of an access port 40 placed through a body wall 15 with an instrument 100 accessing a body cavity 20 therethrough. An operative, distal portion 45 of the instrument extends into the body cavity 20 to an intended site therein to perform a surgical procedure. In some cases, a thick body wall 15 and/or a vastly extended body cavity 20 prevents or reduces the reach and/or unencumbered use of some instruments 100. Moving the access port 40 towards the body wall 15 such that the distal end of the seal housing 41 abuts the entry point 16 in the abdominal wall as illustrated in FIG. 5 compromises the mobility of the access port 40. Consequently, an instrument 100 inserted into the working lumen 42 of such an access port 40 in the condition illustrated in FIG. 5 may not have the desired range of motion. FIGS. 6 and 8 are side views of an instrument 100 inserted in a typical access port 40 with a tall seal housing 41. FIGS. 7 and 9 are side views of a variation of an access port 150 with a shorter, low-profile, seal housing with an instrument 100 inserted therein. As shown in these drawings, the low-profile access port 150 illustrated in FIGS. 7 and 9 provides an increased functional range for the instrument 100 as shown by the greater exposure and hence mobility of the distal end 44 as well as at the proximal end of the instrument 100 compared with the typical access port 40 illustrated in FIGS. 6 and 8.

Referring to both FIGS. 6 and 7, the distal end 47 of the cannula portion 46 is approximately at the same depth inside the patient in each of the FIGS. 6 and 7, with the cannula portions 46 being approximately the same length. At the proximal end 48, the cannula extends the same height from the point of entry 16. However, due to the lower profile of the access port 150 there is more room for the instrument 100 to be manipulated at the proximal end while maintaining the same mobility at the distal end as can be seen in FIG. 7 when compared with the access port with the tall seal housing 41 depicted in FIG. 6 where the instrument mobility is curtailed. In FIG. 7, the instrument 100 can be moved further distally; whereas, the instrument in FIG. 6 cannot be moved distally without also moving access device further distally and thereby affecting the distal mobility because the instrument 100 abuts the proximal end of the seal housing 41. This limited mobility affects the types of instruments that can be employed, in particular, instruments that have a complex articulating distal end 44 as shown or that require more space to be manipulated at the proximal end.

Referring to both FIGS. 8 and 9, the low profile seal housing 150 and the tall seal housing are both shown to abut the entry point 16. The low profile seal housing 150 permits the instrument 100 more mobility to move to a greater depth inside the patient when compared with the tall seal housing 41 of FIG. 8. Of course, more of the distal end 44 of the instrument is advantageously exposed from beyond the cannula portion 46.

Referring now to FIGS. 10-20, various views of an access device 150 with a low profile seal housing according to the present invention are provided. The access device 150 comprises a longitudinal axis extending from a proximal end to a distal end thereof. A seal housing 200 is disposed at the proximal end. A cannula 151 extends distally from the seal housing 200. An instrument access channel extends from the proximal end to the distal end of the access device 150, which is substantially coincident and coaxial with the longitudinal axis in the illustrated variation. The cannula 151 and the seal-housing 200 are sized and configured such that the access device 150 has a low profile and/or short height. Some variations of the access device 150 also exhibit at least one of light weight and simplified construction.

Figure 13:
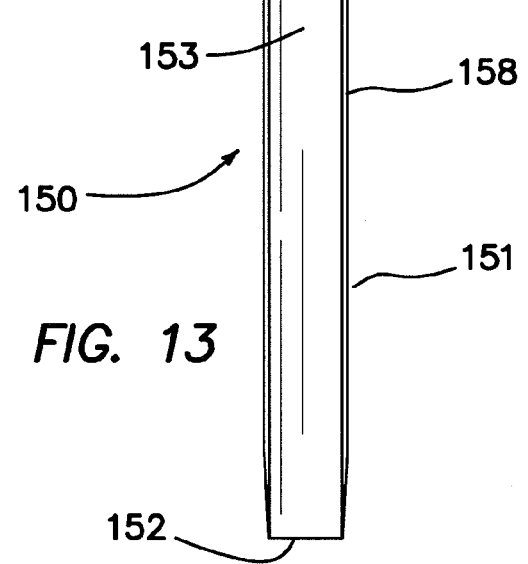
FIG. 13 is a side cross-sectional view of a surgical access port according to the present invention.
Figure 14:
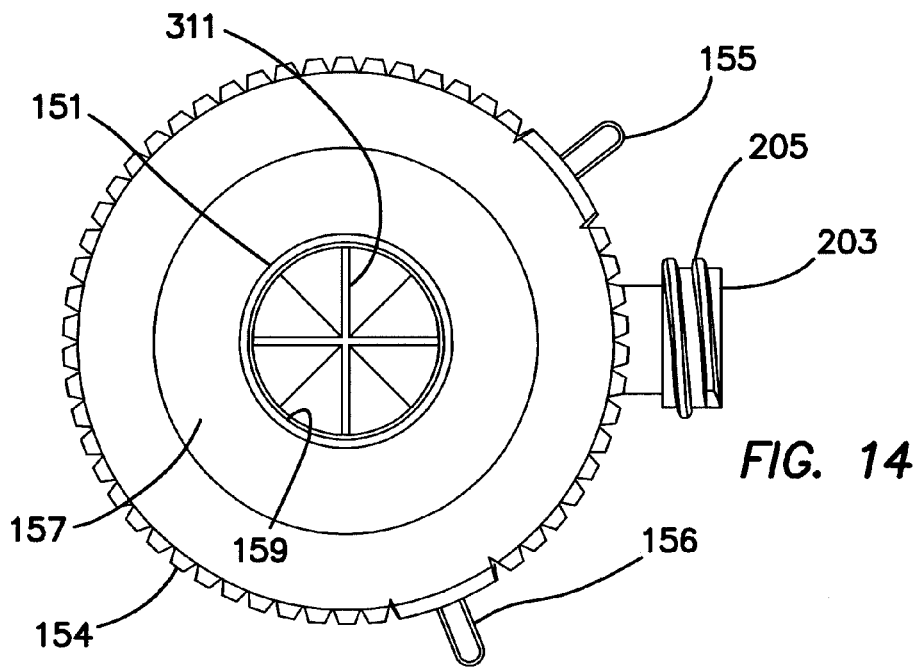
FIG. 14 is a bottom view of a surgical access port according to the present invention.

With particular reference to FIG. 13, which is a side cross section of the access device 150, the cannula 151 comprises an elongate portion 158, sized and configured to penetrate through tissue such as a body wall and is adapted to mate with an obturator (not shown) that is inserted through the lumen 153 to extend out from the distal end 152. The elongate portion 158 has an inner diameter dimensioned to accommodate a range of instrumentation for which the access port 150 is designed. The cannula 151 comprises a distal end 152, a proximal end 157, and a lumen 153 extending therebetween and through which the instrument access channel extends. In the illustrated variation, the distal end 152 is tapered and/or beveled, which facilitates placement of the access device 150 through a body wall. The proximal end 157 of the cannula 151 flares out in a portion in which the cross-sectional area of the lumen 153 is relatively larger than the distal portion of the cannula 151. The proximal end 157 also engages a distal end of the seal housing 200 at a ledge formed in the base 154 of the cannula proximal portion. The lumen 153 extends from the distal end 152 of the cannula to a base 154 at the proximal end 157 thereof. The lumen 153 is fluidly connected to an open plenum 274 in the seal housing 200.

In some variations of the surgical access device 150, the cannula 151 is releasably coupled to the seal housing 200. In other variations, the cannula 151 is not releasably coupled to the seal housing 200. For example, in some variations, the cannula 151 is not designed for release from the seal housing 200 after they are coupled together. Some variations comprise a plurality of cannula 151 in a range of sizes, each of which is dimensioned to couple to a common seal housing 200. For example, some variations comprise a plurality of cannula 151, each of which accommodates a different range of instrument diameters, for example, up to about 5 mm, up to about 8 mm, up to about 11 mm, up to about 12 mm, or up to about 15 mm. Some variations comprise cannula 151 of different working lengths, for example, with working lengths of about 55 mm, about 75 mm, about 100 mm, or about 150 mm, for example. Interchangeability permits the cannula portion 151 to be sterilized and re-used.

Figure 15:
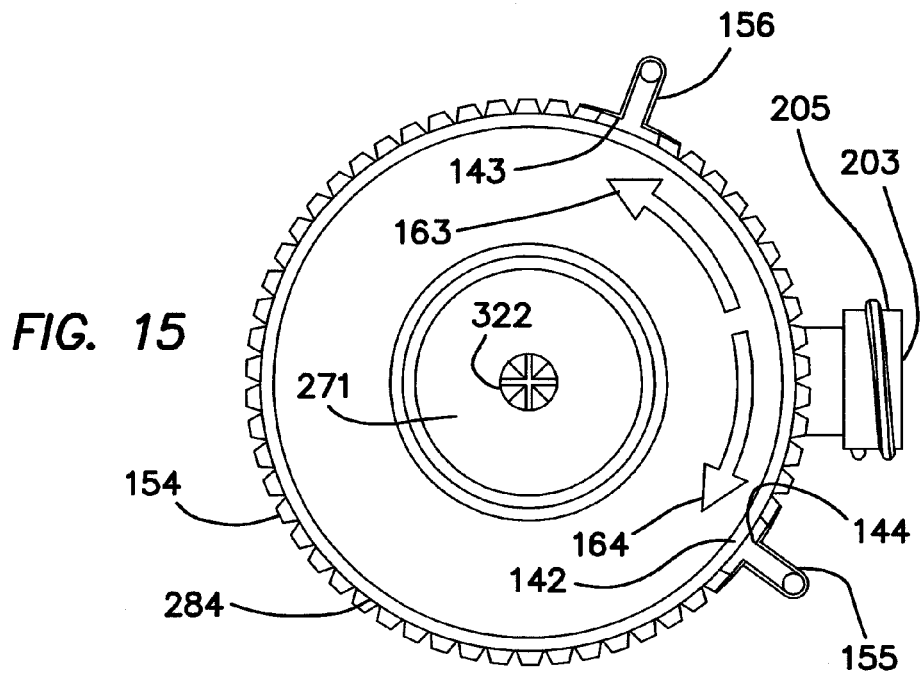
FIG. 15 is a top view of a surgical access port according to the present invention.
Figure 16:
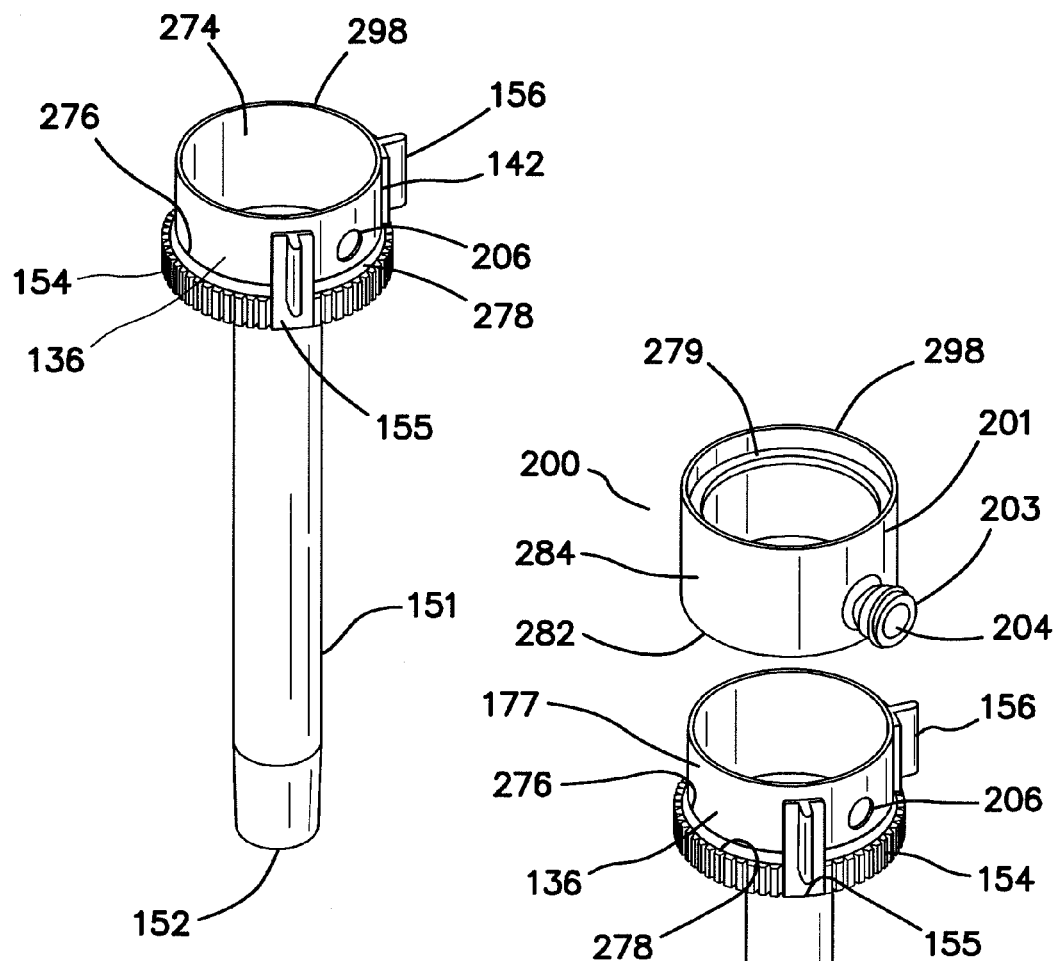
FIG. 16 is a perspective top view of a cannula portion of a surgical access port according to the present invention.
Figure 17:
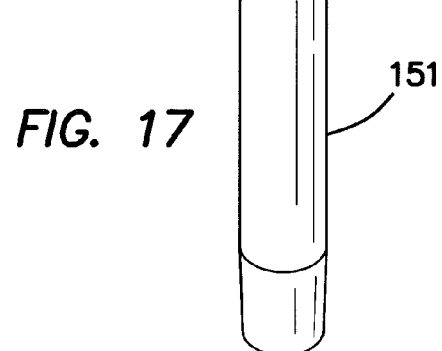
FIG. 17 is an exploded perspective top view of the cannula portion and a seal housing portion of a surgical access port according to the present invention.
Figure 20:
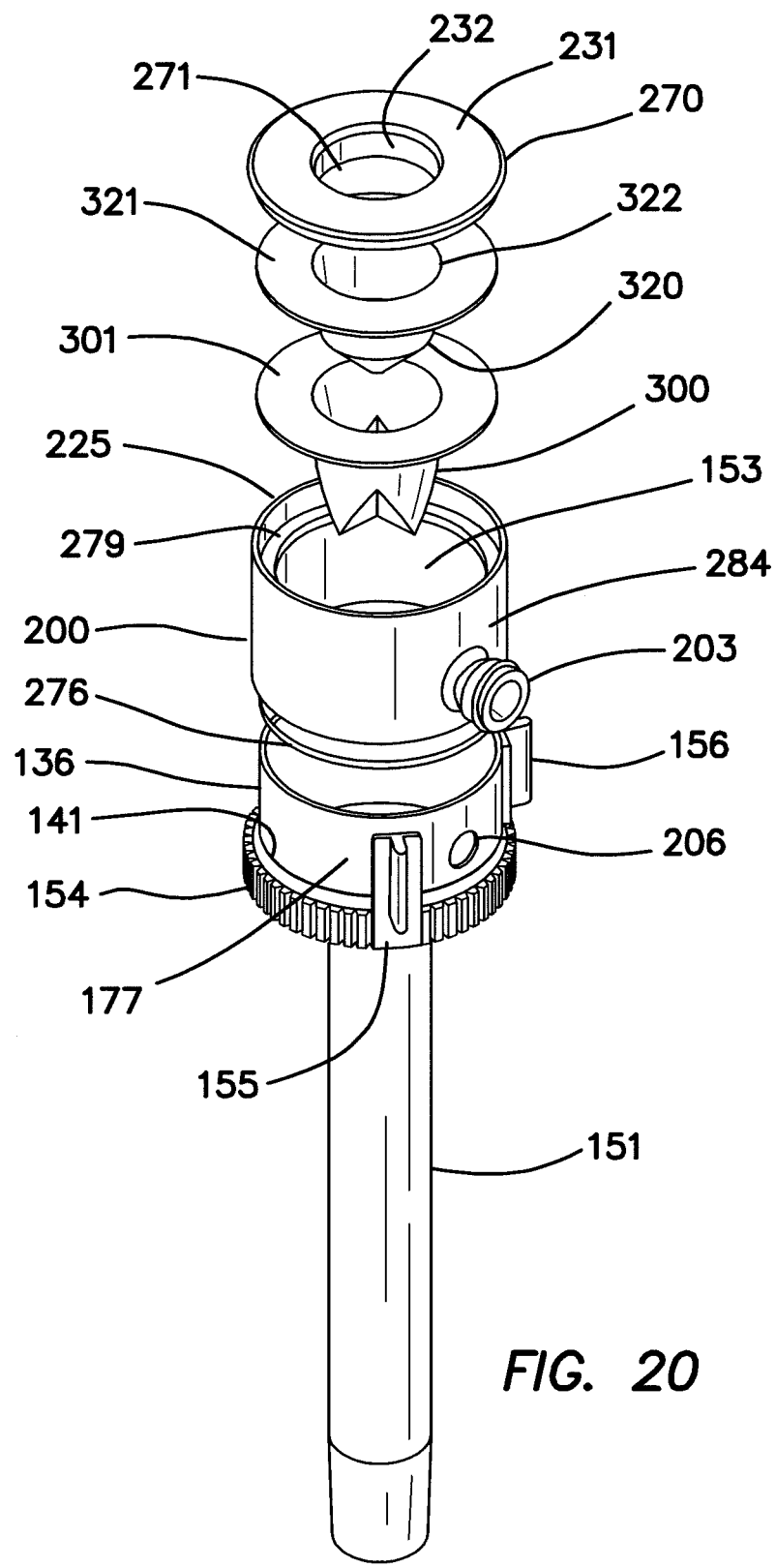
FIG. 20 is an exploded perspective view of a surgical access port according to the present invention.

Still referencing FIGS. 10-20, the seal housing 200 in the illustrated variation comprises a generally cylindrical body 201 comprising a distal end 282, a proximal end 298, and a midsection 284. The distal end 282 engages the proximal portion 157 of the cannula. As shown in FIG. 20, the midsection 284 of the seal housing 200 comprises a cylindrical wall 284 slidingly and rotatably disposed around a coaxial proximal cylindrical side wall 136 of the cannula 151. As best seen in FIGS. 13 and 17, a distal end 282 of the cylindrical wall 284 of the seal housing 200 contacts a ridge or shelf 278. The cylindrical wall 284 of the seal housing 200 sealingly contacts the proximal cylindrical wall 136 of the cannula, thereby substantially preventing gas flow therebetween, as will be apparent from the description below.

With particular reference to FIGS. 17-20, a proximal, seal-housing-engaging portion 177 of the cannula 151 is an enlarged portion of the cannula 151 having a larger cross-sectional area. This enlarged portion 177 is integrally formed with the cannula 151 or may be connectable thereto. The proximal, seal-housing engaging portion 177 is cylindrical and configured to engage with the seal housing 200 in a coaxial manner with the seal housing 200 encompassing the enlarged portion 177 of the cannula 151. The seal housing 200 slides over the enlarged portion 177 engages the seal-housing 200, providing a substantially gas-tight arrangement. An O-ring 276 disposed between the seal-housing-engaging portion 177 of the cannula 151 and the seal-housing 200 provides the substantially gas-tight seal, as well as a detent retention feature. The distal end 282 of the seal housing 200 is disposed within recess or slot 278 of the cannula 151 and is configured to connect thereto such that relative rotation of the two elements is permitted. For example, the recess or slot 278 is formed with an undercut (not shown) to snap fit with a lip (not shown) formed on the seal housing 200. In the illustrated variation, the O-ring is captured in a groove 141 disposed on a proximal cylindrical wall 136 of the cannula. The O-ring 276 also permits the cannula 151 to be manually separated from the seal-housing 200. The cylindrical wall 284 of the seal housing 200 is arranged concentrically around the proximal cylindrical wall 136 of the cannula 151 inside a gap 142 between the cylindrical wall 136 and projections 155, 156. Projections 155, 156 extend radially outwardly from the cannula base 154 and extend proximally.

Figures 18, 19:
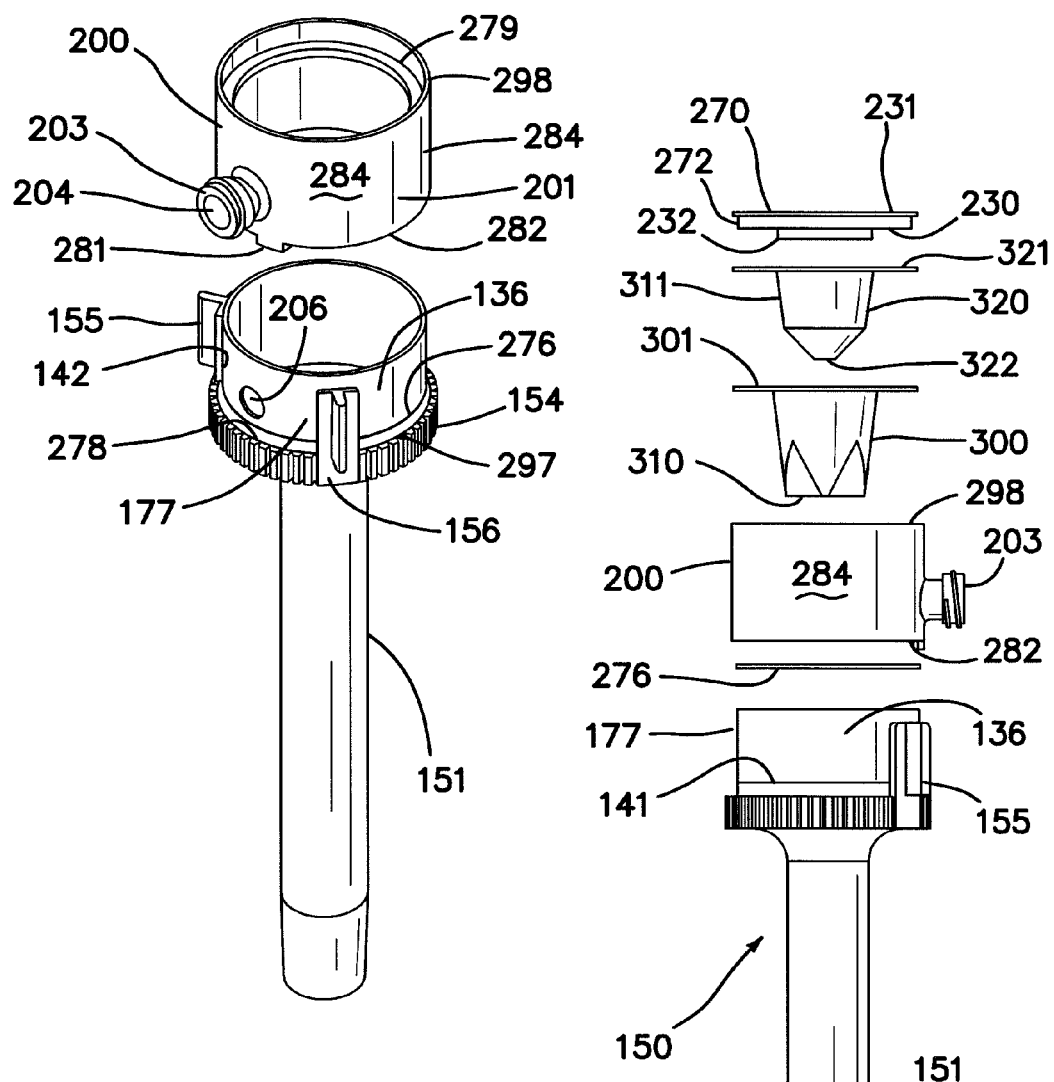
FIG. 18 is another exploded perspective top view of the cannula portion and the seal housing portion of a surgical access port according to the present invention.
FIG. 19 is an exploded side view of a surgical access port according to the present invention.

As best seen in FIGS. 19 and 20, which are an exploded side and perspective views, respectively, of the access device 150, a plurality of seal members 300 and 320 are received within the cylindrical wall 284 of the seal housing 200 and captured or trapped therein by a cap or end member 270 closing the top of cylindrical wall 284 of the seal-housing 200. As illustrated in FIGS. 17, 18 and 20, the seal housing 200 comprises the ridge or shelf 279 extending inwardly from a wall 284 thereof. Some variations of the ridge or shelf 279 comprise a tractive surface and/or features that contact and secure the seal members 300 and 320.

In the illustrated variation, a first seal member 320 a generally frustoconical elastomeric member with an opening 322 sized and configured to conform to and seal around the shaft of an instrument inserted therethrough, which is also referred to as an instrument seal. A second seal member 300 comprises an elastomeric check-valve or duck-bill valve sized and configured to seal the lumen 153 and plenum 274 of the access port 150 when no instrument is within the working channel or lumen 153, which is also referred to as a zero seal. Each seal member 320 and 300 further comprises a radially extending portion 321, 301, respectively, sized and configured to allow the seal members 300 and 320 to float and/or pendulate, for example, responsive to and following the movement of an inserted instrument within the working channel 153 of the access port 150. The radially extending portions 321, 301 of one or more of the first seal member 320 and second seal member 300 are captured between the cap 270 and shelf 279 and depending portions 310, 311 of seals 300, 320 pendulate therefrom. Other variations comprise a different configuration of seals, for example, a single seal that serves as both an instrument seal and a zero seal. An example of such a seal is a gel seal.

Figures 21, 22:
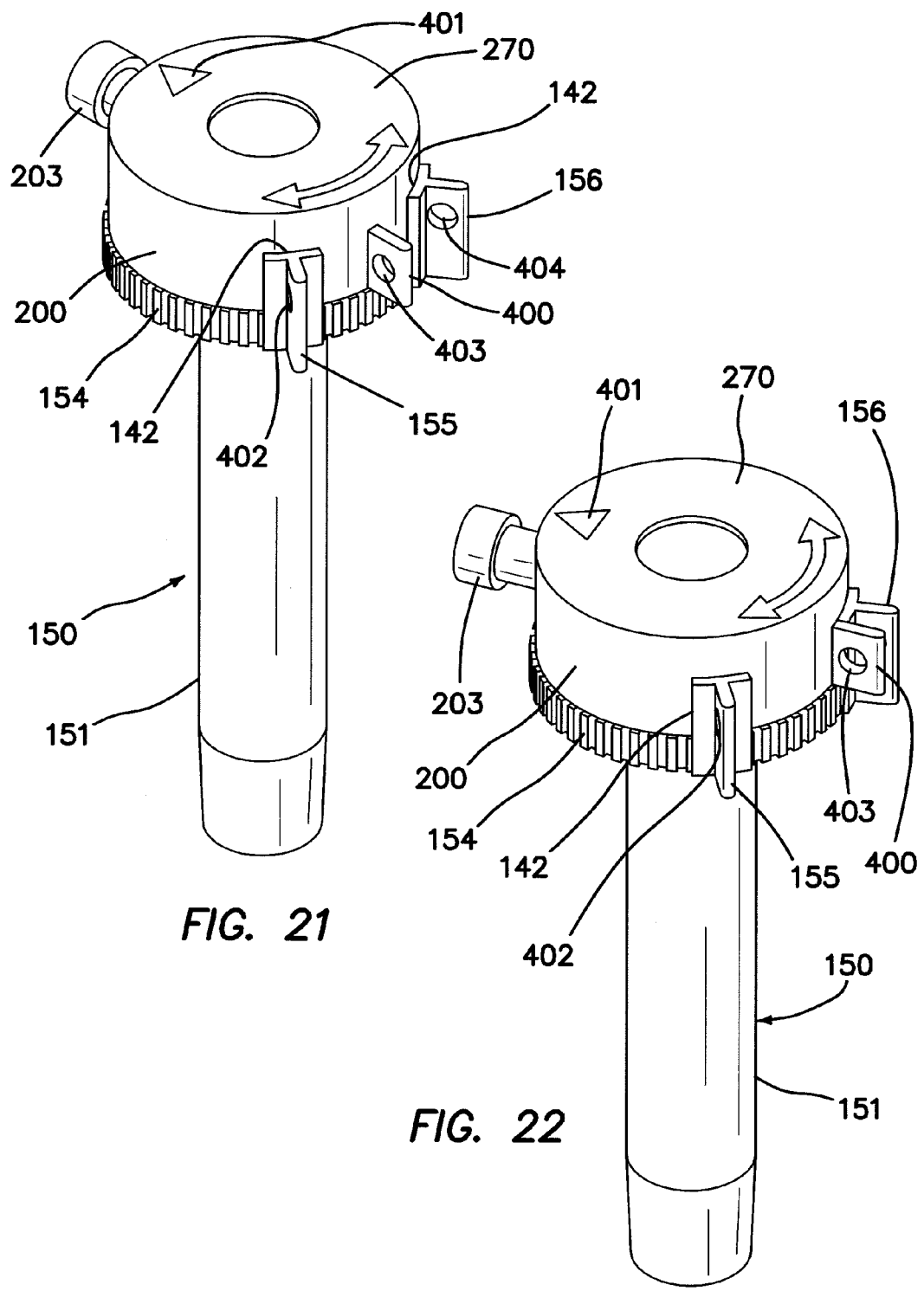
FIG. 21 is a perspective top view of a surgical access port according to the present invention.
FIG. 22 is a perspective top view of a surgical access port according to the present invention.

As best seen in FIGS. 13, 19 and 21, in the illustrated variation, the cap or end member 270 comprises a generally flat member that is sized and configured to snap into and/or engage the proximal portion of the seal-housing 200 in a connecting fashion and to secure or hold the associated seal members 300 and 320 in place within the access port 150. The cap or end member 270 comprises a seal-housing engaging portion 272, a distal-facing surface 230, a proximal-facing surface 231, and a generally cylindrical projection 232 defining a central bore 271. The central bore 271 comprises a through-hole sized and configured to allow passage of surgical instruments therethrough. For example, some variations of the central bore 271 accommodate instruments of from about 3.5 millimeters to about 16 millimeters in diameter. Therefore, the central bore 271 in the cap 270 is at least about 16 millimeters, for example.

A connecting hub or fitting 203 sized and configured for coupling to a gas supply is disposed on the mid-section 284 of the seal housing. In the illustrated variation, the hub 203 extends radially outwardly from the seal housing 200. In other variations, the hub 203 has another configuration, for example, extending longitudinally, tangentially, or in another direction. In the variation illustrated in FIG. 10, the connecting hub 203 comprises a standard, male connecting portion 205, for example, a Luer fitting, and a through-lumen 204. The through-lumen 204 reduces restriction of gas flow therethrough with the device in an open configuration, as discussed below.

As best seen in FIG. 18, the distal end 282 of the seal-housing 200 comprises a projection 281 that corresponds with and fits inside a recess or slot 278 in the base 154 of the cannula. In the assembled access port 150, the projection 281 fits into the recess 278, which has an angular width greater than an angular width of the projection 281, thereby, conferring the seal housing 200 with a degree of rotation relative to the cannula 151 around the longitudinal axis. The seal-housing 200 is rotatable between a first position and a second position. In a first or open position, the through lumen 204 of an inflation port 203 disposed on the midsection 284 of the seal-housing aligns with a side opening or hole 206 in a side wall 136 at the proximal portion 297 of the cannula, thereby fluidly connecting the inflation port 203 with the plenum 274. Rotating the seal housing 200 to the second or closed position offsets lumen 204 of the inflation port from the side opening 206, thereby fluidly isolating the inflation port 203 from the plenum 274. Consequently, an angle of rotation of the seal housing 200 between the first position and the second position is greater than the larger of the angle subtended by lumen 204 of the inflation port and the side opening 206 in the side wall of the cannula. The inflation port 203 on the seal housing 200 and the side opening 206 in the side wall 136 of the cannula together define a fluid valve, which is integrated with the seal housing 200 and cannula 151 creating a access port having a low profile. The illustrated arrangement of an aligned and non-aligned lumen 204 and opening 206 eliminates bulky and complex valves, stopcocks, and the like and permits a shorter seal housing and greater range of motion and mobility of the access port as well as reducing manufacturing costs.

As illustrated in FIGS. 14-17, the connecting hub 203 is integrally manufactured with the seal housing 200 of the access port 150 rather than a separate part assembled therewith. In some variations, the cannula 151 and the seal housing 200 comprise rigid plastic, thereby facilitating integrally molding or forming the connecting hub 203 in the manufacture of the seal-housing 200. In some variations comprising a metal seal-housing 200, the connecting hub 203 is separately manufactured and subsequently secured or coupled to the seal-housing 200. In some variations, the connection hub 203 is adjustable, for example, pivotable and/or rotatable relative to the seal housing 200.

Those skilled in the art will understand that other variations comprise other arrangements. For example, in some variations, the projection 281 is disposed on the cannula 151 and the recess or slot 278 on the seal housing 200. Other variations comprise a pair of stops such as projections 155, 156 that together with the projection 281 limit the rotation of the seal housing 200. In the variation illustrated in FIG. 18, the projection 281 extends longitudinally. In some variations, the projection 281 extends radially inward and/or outward. Similarly, in some variations, the side wall 136 is a component of cannula 151 rather than the seal housing 200.

In the illustrated variation, as best seen in FIG. 16, the access device 150 comprises a first elongate projection 155 and a second elongate projection 156, each of which is connected to the base 154 and extends axially upwardly from the base 154 of the cannula 151 toward the proximal end thereof forming a gap 142 between the grip element 155, 156 and the cylindrical wall 136 of the cannula. Into this gap 142, the seal housing 200 is inserted and configured to closely conform and rotate about the cylindrical wall 136. As best seen in FIG.

15, which is a top view of the access device 150, inwardly facing surfaces 143 and 144 of the projections 156 and 155, respectively, are radially spaced from the cylindrical wall 284 of the assembled seal housing 200, thereby permitting the seal-housing 200 to rotate freely around the longitudinal axis of the cannula 151. The projections 155 and 156 are sized and configured to provide the cannula 151 with a traction feature, as discussed below. Applying a compressive or force tangential to the cylindrical wall 284 of the seal housing 200 between one of the projections 155 and 156, and the inflation hub 203, for example, by grasping between a user's thumb and index finger, or otherwise squeezing/pressing one of the projections 155, 156 and inflation hub 203 together rotates the seal housing 200 relative to the cannula 151, thereby converting the access device 150 between the open and closed configurations described above, in which the opening 206 and the lumen 204 of the inflation port are aligned and offset, respectively. The opening 206 in the side wall 136 of the cannula 151 of the access port 150 is adjusted to align with the lumen 204 of the inflation port 203 of the seal-housing 200, and/or the seal-housing 200 is adjusted to align the lumen 204 of the inflation port 203 with the side opening 206 of the cannula 151 in converting the access device 150 to the open configuration. The aligned lumen 204 and opening 206 fluidly connect a gas supply coupled to the inflation port 203 with the main lumen 153 of the cannula 151 for movement of fluid across the cannula such as for insufflation of a body cavity. In one variation, the second projection is not connected to the cannula but is formed by the outwardly extending inflation port and is coincident with the seal housing. In another variation, the angle subtended by the first and second projections is less than 90 degrees defining their maximum degree of separation. Also, in another variation, the invention is not limited to relative rotation of the seal housing and cannula to effect alignment of the inflation port and opening. For example, the seal housing can slide up and down relative to the cannula to align the inflation port of the seal housing with the opening in the cannula between an open position in which fluid is permitted to flow across the cannula and seal housing into the lumen and a closed position in which fluid is prevented from flowing across the cannula and seal housing and into the lumen. Of course, partial alignment of the opening with the inflation port can be effected to regulate the rate of fluid flow.

The variation illustrated in FIG. 15 comprises indicia 163 and 164 indicating the state of the integral valve and/or guiding the user in converting the valve between the open and closed states. For example, in some variations, the indicia are color-coded or the like, thereby indicating the current state of the valve, its alignment or rate of flow.

Figures 23, 24:
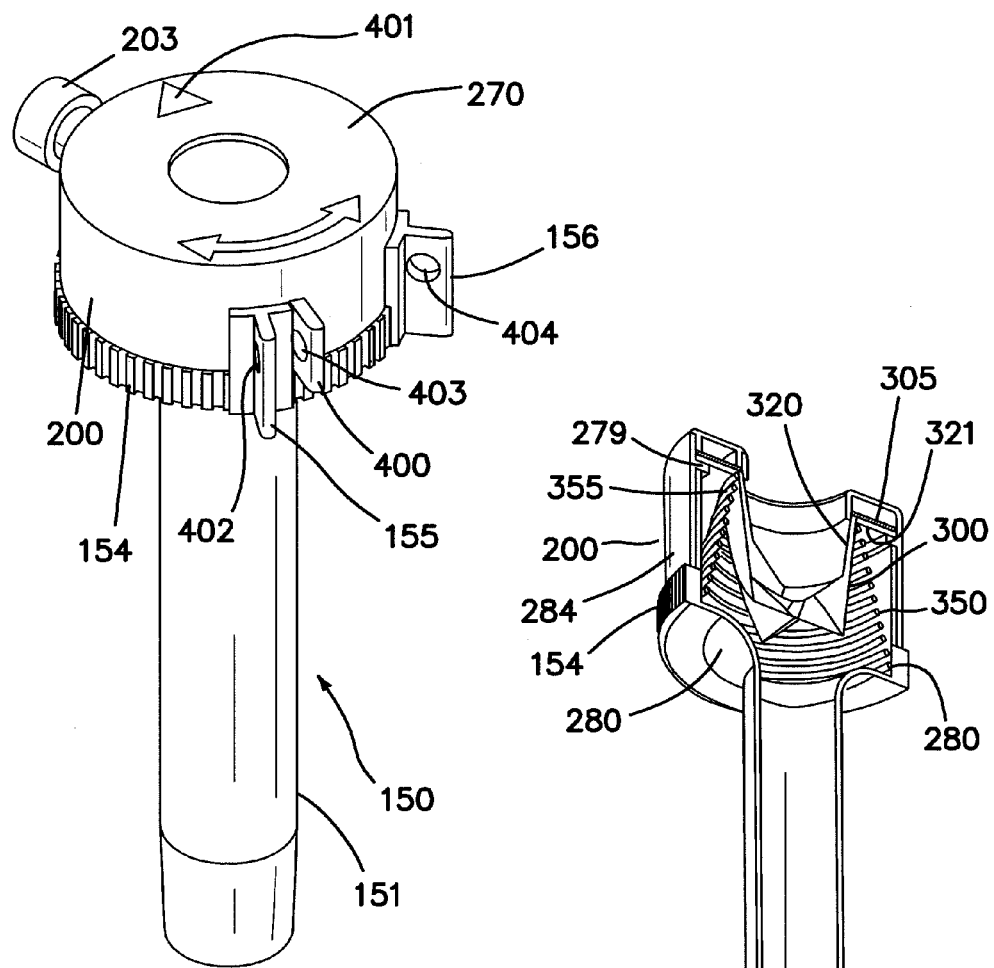
FIG. 23 is a perspective top view of a surgical access port according to the present invention.
FIG. 24 is a perspective side cross-sectional view of a surgical access port according to the present invention.
Figure 25:
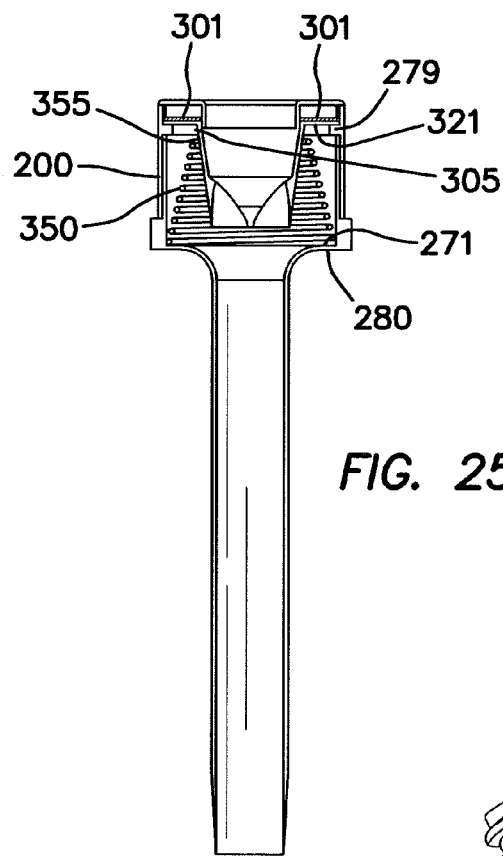
FIG. 25 is a cross-sectional side view of a surgical access port according to the present invention.
Figure 26:
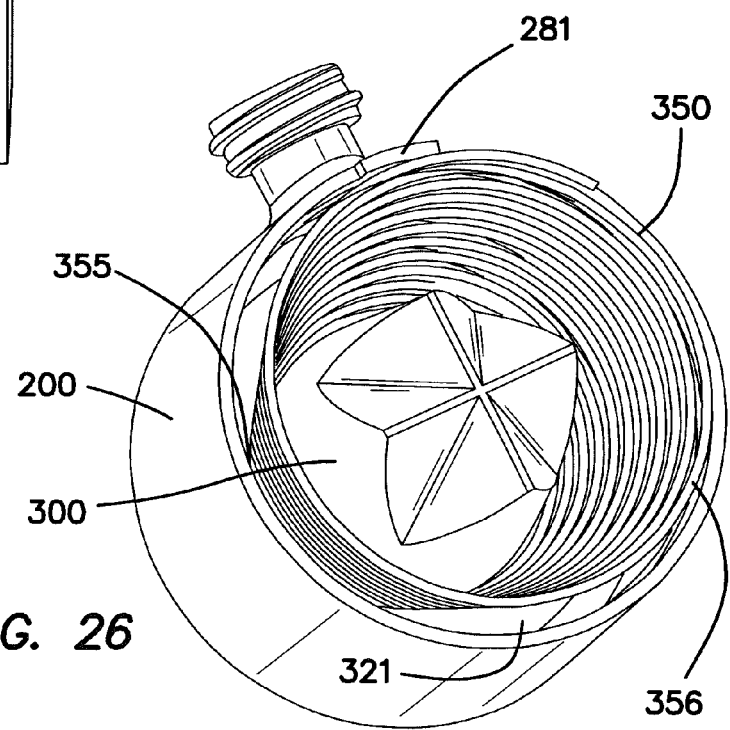
FIG. 26 is a bottom perspective view of a seal-housing and tapered retention member of a surgical access port according to the present invention.
Figure 27:
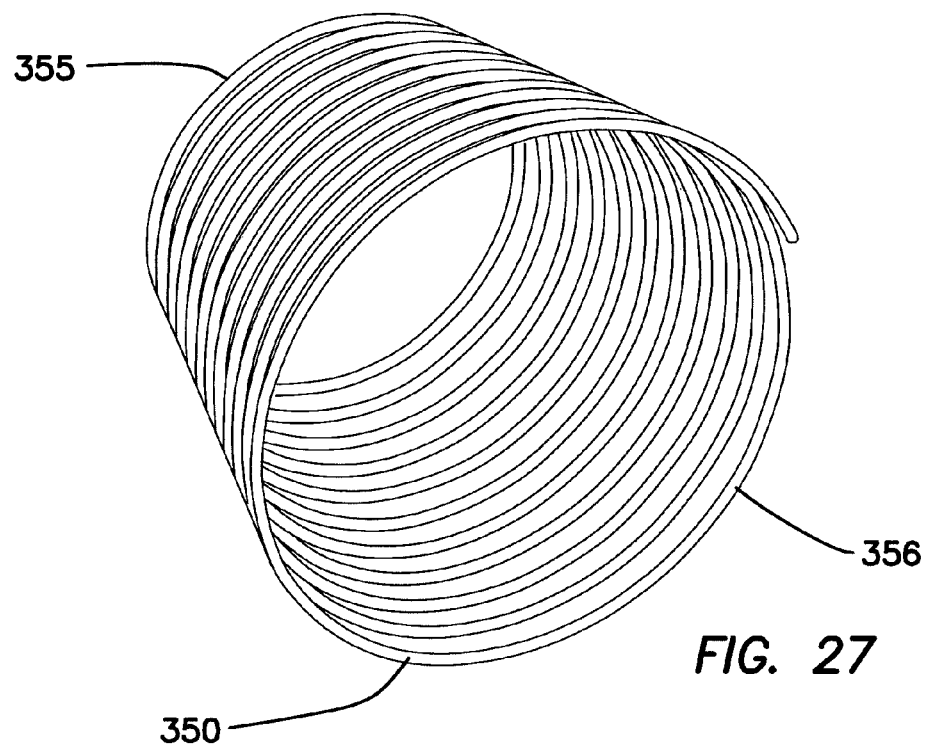
FIG. 27 is bottom perspective view of a tapered retention member of a surgical access port according to the present invention.
Figure 28:
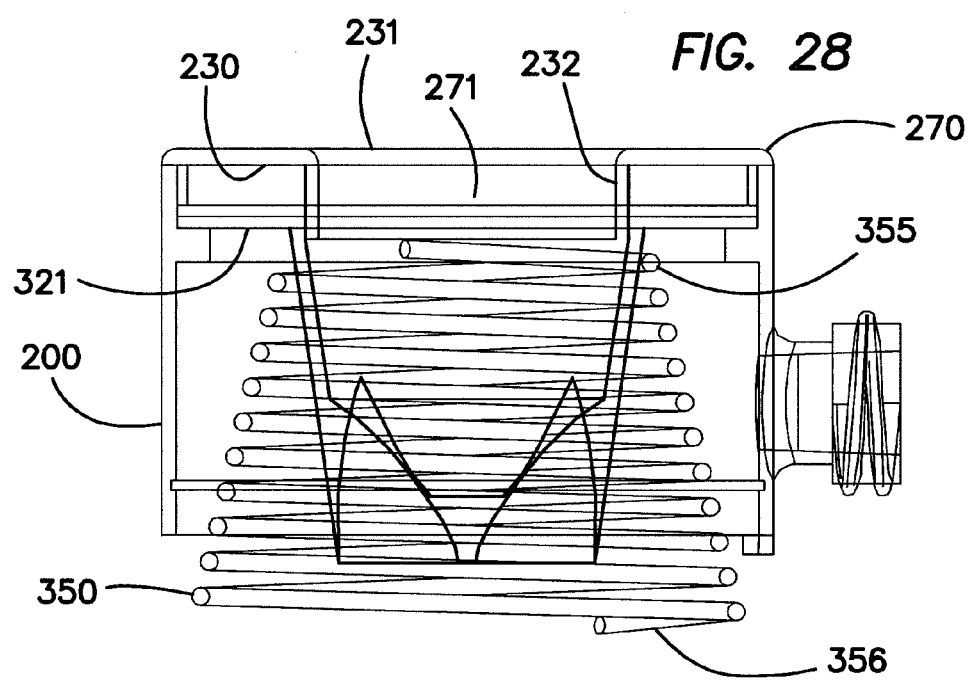
FIG. 28 is a side cross-sectional view of a seal-housing and tapered retention member of a surgical access port according to the present invention.

Turning now to FIGS. 21-23, there is shown another variation of the low profile access port 150 that illustrates a first projection 155 connected to base 154 of the proximal end of the cannula 157 that projects radially outwardly and extends proximally and is spaced apart from the cylindrical wall 136 of the cannula 151 to form a gap 142. As described above, the seal housing 200 slides over the cylindrical wall 136 of the cannula in a coaxial manner to rest inside the gap 142 between the cylindrical wall 136 first projection 155 and into a snap-fit engagement with the cannula contacting a ridge or shelf with a seal such as an O-ring as described above with the previous variations. A second projection 400 is formed on the seal housing 200. The second projection 400 extends radially outwardly from the outer surface 284 of the seal housing. As shown by indicia 401 in FIG. 21, the opening 206 in the side wall is in alignment with the connecting hub lumen 203 resulting in a first open position in which the lumen of the hub 203 is in fluidic communication with the plenum inside the seal housing 200 and gas may flow into the access port. The application of a compressive force or a force tangential to the cylindrical wall 284 of the seal housing 200 such as by pressing the first projection 155 and the second projection 400 together such as by placing one finger on the first projection 155 and another finger on the second projection 400 and squeezing or pressing rotates the seal housing 200 relative to the cannula 151, thereby converting the access device 150 from an open to a closed configuration as shown in FIG. 23 wherein the projections 155, 400 are close together. Of course to open the valve again force is applied to space apart the projections 155, 400. Apertures 402, 403 are formed in the first and second projections 155, 400, respectively, and adapted for robotic control and manipulation of the projections into the open and closed positions. In contrast to the variation shown in FIGS. 10-20, the second projection 400 in the variation shown in FIGS. 21-23 is not the connecting hub 203 but a separate projection formed on the seal housing. The open valve position indicated by indicia 401 being in alignment with the hub 203 can correspond with the second projection 400 being midway between the first projection 155 and an additional third projection 156 as shown in FIG. 21, or alternatively, the open valve position indicated by indicia 40 being aligned with the hub 203 can correspond with the second projection 400 being adjacent to the third projection 156 as shown in FIG. 22 or, of course, adjacent to the first projection 155. Either way, force is applied to move the projections 156, 400 and rotate the seal housing 200 relative to the cannula 151 to open the valve as shown in FIG. 22, which may also correspond to a closed position in another variation. Likewise force is applied to move the projections 400 relative to the other one of the two projections 155, 156. Of course, force may be applied to separate or spread apart the projections 400, 156 from the position shown in FIG. 22 to a position shown in FIG. 21.

In another variation, the surgical access device includes an elongate tubular cannula having a lumen extending between an open proximal end and an open distal end. A seal housing is connected to the proximal end of the cannula. The seal housing includes an access channel at the proximal end arranged to be coaxial with the lumen of the cannula and providing access to the cannula lumen. The seal housing includes an outer side wall having a first opening movable relative to an inner side wall having a second opening. At least one seal is disposed inside the seal housing. The first and second openings are configured to align at least in part to fluidly connect the cannula lumen across the seal housing with outside the device. A port on the outer surface of the outer side wall at the location of the first opening is adapted to connect to a source of fluid under pressure for delivering fluid to and from the cannula lumen along the first and second openings when the first and second openings are at least in part aligned. The degree of fluidic communication can be regulated by selective alignment of the first and second openings. For example, partial alignment will provide low fluid flow relative to full alignment of first and second openings having coincident geometries which will provide greater fluid flow. The outer side wall is movable relative to the inner side wall between an open configuration and a closed configuration. In the open configuration, the first opening is in alignment at least in part with the second opening, thereby, fluidly connecting the cannula lumen across the seal housing. In the closed configuration, the first opening is offset from the second opening, thereby, closing fluidic communication across the seal housing. The seal housing includes a plenum distal to the at least one seal disposed inside the seal housing. The first and second openings are located along the seal housing for fluidic communication with this plenum which in turn is in fluid communication with the cannula lumen such that fluid flow across the seal housing into the plenum and into the cannula lumen. The outer side wall of the seal housing is longitudinally movable or rotatably movable relative to the inner side wall. The inner side wall and outer side wall are sealingly engaged such as by an O-ring seal such that no fluid escapes between the first and second side walls except through aligned first and second openings. The top of the seal housing includes a cap that includes an opening coaxial with the access channel of the seal housing. An internal ledge formed on the inside of the seal housing supports radially outwardly extending portion of the at least one seal and the cap captures the radially outwardly extending portion between the ledge and cap. The at least one seal includes a depending portion that is free to pendulate inside the seal housing and a spring biases both longitudinal and lateral translation of the seal. The spring may be tapered as will be described below.

The illustrated configuration defines an integral valve for the inflation port 203, thereby, obviating the need for an external valve or stopcock, thereby, reducing the radial size of the seal housing 200. The reduced radial size provides greater freedom in positioning the access device 150, for example, tilted at a greater angle, and/or closer to another instrument and/or access device. In the illustrated variation, opening and closing the integral gas valve is a one-handed operation, in contrast with some external valves in which two hands are typically used, thereby permitting a user to opening or close the gas valve while manipulating an instrument therein. Moreover, the traction features permit a user to position the access device 150, for example, advancing, withdrawing, rotating, and/or tilting, while opening and/or closing the gas valve.

Those skilled in the art will understand that in other variations, the seal housing is disposed within and sealingly rotatable within side wall of the cannula instead of around the side wall of the cannula. In some of these variations, the connecting hub is disposed on the side wall of the cannula and the side opening is disposed on the seal housing.

FIGS. 24-28 illustrate another variation of an access device that is similar to the variation described above and illustrated in FIGS. 10-23. The illustrated variation further comprises a resilient support member 350 disposed between the seal members 300,320 and the cannula 280 and seal housing 200. In the illustrated variation, the resilient member 350 comprises a tapered, helical coil spring disposed around and surrounding the seal members 300 and 320. A smaller diameter, proximal end 355 of the resilient member 350 contacts and surrounds proximal portions 305 of the seal members 300 and 320, while a larger diameter, distal end 356 contacts and rests upon a proximally facing surface 271 of the cannula base floor 280. The spring 350 is disposed under a light compressive load between a first end 355 and a second end 356 thereof when placed inside the seal housing 200. The proximal end 355 of the resilient member 350 abuts the radially extending portion 301 of seal member 300 which in turn contacts the radially extending portion 321 of seal member 320. The distal end 356 abuts the proximally facing surface 271 of the cannula base floor 280. In use, when an instrument is inserted into the working lumen, friction between the instrument and the seal will move the seal in the same direction as the instrument and result in stretching of the seal material and/or deflection of the seal material near its point of fixation along the radially extending portions 301, 321 or anywhere on the seals 300, 320. With the resilient member 350, the narrow proximal end 355 closely surrounds the portion of the seal that depends distally into the lumen. With the resilient member 350 slightly compressed inside the seal housing a spring bias force is applied onto the radially extending portions 301, 321 to bias any force in a distal direction from an inserted instrument. In use, inserting an instrument through the seal members 300 and 320 applies a linear load on the spring 350, thereby, compressing the spring 350, which reduces or prevents excessive stretching of the radially extending portions 301, 321 of the seal members 300, 320, respectively. Also, when the instrument is removed, that is, moved in a proximal direction, friction between the seal and the instrument may tend to pull the seal along with the instrument in a proximal direction. The wide distal end of the resilient member 350 permits pendulation of the seal at the distal end but also the resilient member 350 biases extreme deflection or pendulation toward the longitudinal axis of the lumen and thereby reducing frictional forces between the seal and instrument or reducing stretching and potential tearing of the seal material. After the linear load is removed, the spring 350 returns to the original, lightly-compressed condition, thereby, allowing the seal members 300 and 320 to pendulate freely. Those skilled in the art will understand that in other variations, the resilient member comprises another structure known in the art, for example, an elastomeric element, a pneumatic element, a hydraulic element, and the like, either individually, or in combination.

While certain variations have been particularly shown and described with reference to exemplary variations thereof, it will be understood by those of ordinary skill in the art that various changes in form and details may be made therein without departing from the spirit and scope thereof as defined by the following claims.

I claim:

1. A surgical access device comprising:
   an elongate tubular cannula having a lumen extending between a proximal end and a distal end and defining a longitudinal axis;
   a seal housing rotatably connected to and partially surrounding the proximal end of the cannula;
   a seal assembly comprising at least one seal disposed in the seal housing; the at least one seal includes a radially extending portion and a depending portion; the at least one seal being connected to the seal housing such that the at least one seal is fixed to the seal housing at the radially extending portion and the depending portion is allowed to pendulate;
   an access channel defining a longitudinal axis extending through the seal assembly and the lumen of the cannula from the proximal end to the distal end;
   a resilient member comprising a helical coil spring having a proximal end and a distal end and defining a longitudinal axis; the coil spring being located inside the seal housing between the seal assembly and the seal housing such that the coil spring surrounds the depending portion of the at least one seal; and
   a cap abutting a proximal end of the seal housing.

2. The access device of claim 1 wherein the resilient member is configured to bias translation of the at least one seal.

3. The access device of claim 1 wherein the longitudinal axis of the coil spring is coaxial with the longitudinal axis of the lumen.

4. The access device of claim 1 wherein the coil spring is tapered such that the proximal end of the coil spring is narrower than the distal end of the coil spring.

5. The access device of claim 1 wherein the proximal end of the coil spring is positioned against the radially extending portion to bias the radially extending portion.

6. The access device of claim 1 wherein the proximal end of the coil spring contacts the radially extending portion and closely conforms around the depending portion to bias lateral deflection of the depending portion.

7. The surgical access device of claim 1 wherein the coil spring is disposed inside the seal housing under a light compressive load between the proximal end and the distal end of the coil spring.

8. The surgical access device of claim 1 wherein the cannula includes a base floor and the distal end of the coil spring abuts the cannula base floor.

9. The surgical access device of claim 1 wherein the coil spring reduces excessive stretching of the at least one seal when an instrument is inserted through the at least one seal.

10. A surgical access device comprising:
an elongate tubular cannula having a lumen extending between a proximal end and a distal end; the cannula having a side wall that extends radially outwardly relative to the distal end of the cannula thereby forming an enlarged portion at the proximal end; and an opening extending through the side wall at the enlarged portion of the cannula; the side wall at the enlarged portion of the cannula being cylindrical and having a proximal end and a distal end and an outwardly extending ridge defined at the distal end of the side wall at the enlarged portion of the cannula;
a seal housing connected to and coaxial with the proximal end of the cannula and configured to be sealingly movable relative to the side wall; the seal housing having an inflation port extending through the seal housing and configured to align at least in part with the opening in the side wall to fluidly connect the inflation port with the cannula lumen through the opening; the seal housing includes a cylindrical body having a distal end and a proximal end; the seal housing includes a shelf extending inwardly from the cylindrical body; the seal housing partially surrounding the enlarged portion of the cannula in a coaxial manner; the distal end of the seal housing contacting the ridge of the cannula; and
a seal assembly comprising at least one seal disposed in and connected to the seal housing; the at least one seal includes a radially extending portion and a depending portion; the depending portion extending distally from the radially extending portion;
wherein the seal housing is movable relative to the side wall between an open configuration and a closed configuration; in the open configuration, the inflation port is in alignment at least in part with the opening in the side wall fluidly connecting the inflation port and opening with the cannula lumen, and in the closed configuration, the inflation port is offset from the opening in the side wall fluidly isolating the inflation port from the opening in the side wall.

11. The access device of claim 1 wherein the at least one seal is disposed inside the seal housing such that the radially extending portion rests on top of the shelf; and further including a cap closing the proximal end of the seal housing wherein the cap secures the seal assembly within the seal housing; the cap having an opening to the cannula lumen.

12. The access device of claim 1 further comprising a first projection extending radially outwardly from the cannula side wall and a second projection extending radially outwardly from the cannula side wall wherein the access device is convertible between the open configuration and the closed configuration by moving the first and second projections relative to the inflation port.

13. The access device of claim 12 wherein the first projection is adjacent to one side of the inflation port and the second projection is adjacent to the opposite side of the inflation port.

14. The access device of claim 1 further comprising a first projection extending radially outwardly from the cannula side wall and a second projection extending radially outwardly from the seal housing; wherein the access device is convertible between the open configuration and the closed configuration by moving the first projection relative to the second projection.

15. The access device of claim 14 wherein the second projection is formed by the inflation port.

16. The access device of claim 1 further comprising a resilient member comprising a helical coil spring having a proximal end and a distal end and defining a longitudinal axis; the resilient member being located inside the seal housing between the seal assembly and the seal housing; the at least one seal being connected to the seal housing at the radially extending portion such that the proximal end of the coil spring contacts the radially extending portion and the depending portion is allowed to pendulate; and the coil spring encompassing the depending portion of the at least one seal.

17. The access device of claim 16 wherein the longitudinal axis of the coil spring is coaxial with a longitudinal axis of the cannula.

18. The access device of claim 16 wherein the coil spring is tapered, wherein the proximal end of the coil spring is narrower than the distal end of the coil spring.

19. The access device of claim 18 wherein the cannula side wall includes a cannula base floor that extends radially around the cannula lumen; wherein the narrower proximal end of the coil spring contacts the radially extending portion of the at least one seal and the wider distal end of the coil spring contacts the cannula base floor.

20. The access device of claim 16 wherein the resilient member is contained in a lightly compressed condition between the at least one seal and a cannula base floor.

* * * * *